(12) United States Patent
Patel et al.

(10) Patent No.: US 7,687,494 B2
(45) Date of Patent: Mar. 30, 2010

(54) SUBSTITUTED SPIROBENZAZEPINES

(75) Inventors: Mona Patel, Belle Mead, NJ (US);
Philip J. Rybczynski, Branchburg, NJ (US); Min Amy Xiang, Bridgewater, NJ (US)

(73) Assignee: Janssen Pharmaceutica NV (BE)

( * ) Notice: Subject to any disclaimer, the term of this patent is extended or adjusted under 35 U.S.C. 154(b) by 0 days.

(21) Appl. No.: 11/735,149

(22) Filed: Apr. 13, 2007

(65) Prior Publication Data

US 2007/0179128 A1 Aug. 2, 2007

Related U.S. Application Data

(63) Continuation of application No. 10/869,746, filed on Jun. 16, 2004, now abandoned.

(60) Provisional application No. 60/479,378, filed on Jun. 17, 2003.

(51) Int. Cl.
*A61P 9/00* (2006.01)
*A61K 31/55* (2006.01)
*C07D 223/32* (2006.01)

(52) U.S. Cl. .................................. 514/212.02; 540/543

(58) Field of Classification Search ............ 514/212.02; 540/543
See application file for complete search history.

(56) References Cited

U.S. PATENT DOCUMENTS

| | | | |
|---|---|---|---|
| 4,617,302 | A | 10/1986 | Robertson |
| 5,258,510 | A | 11/1993 | Ogawa et al. |
| 5,559,230 | A | 9/1996 | Ogawa et al. |
| 5,663,431 | A | 9/1997 | Di Malta et al. |
| 5,686,624 | A | 11/1997 | Di Malta et al. |
| 5,726,322 | A | 3/1998 | Di Malta et al. |
| 5,728,723 | A | 3/1998 | Di Malta et al. |
| 5,753,715 | A | 5/1998 | Chen et al. |
| 5,849,780 | A | 12/1998 | Di Malta et al. |
| 5,985,869 | A | 11/1999 | Ogawa et al. |
| 7,001,898 | B2 * | 2/2006 | Chen et al. ............. 514/212.02 |
| 7,365,062 | B2 | 4/2008 | Chen et al. |
| 2004/0259857 | A1 * | 12/2004 | Deng et al. .................. 514/217 |
| 2006/0111567 | A1 * | 5/2006 | Chen et al. .................. 540/466 |
| 2007/0117790 | A1 * | 5/2007 | Chen et al. ............. 514/212.02 |
| 2007/0135409 | A1 * | 6/2007 | Chen et al. ............. 514/212.02 |

FOREIGN PATENT DOCUMENTS

| | | | |
|---|---|---|---|
| EP | 0636608 | A | 2/1995 |
| EP | 0640592 | A | 3/1995 |
| EP | 0640592 | B1 | 3/1995 |
| WO | WO 9105549 | A | 5/1993 |
| WO | WO 9407496 | A | 4/1994 |
| WO | WO 9525443 | A | 9/1995 |
| WO | WO 9749707 | A | 12/1997 |
| WO | WO 9937637 | A | 7/1999 |
| WO | WO 02/02531 | | 1/2002 |
| WO | WO 2005/000819 | | 1/2005 |

OTHER PUBLICATIONS

Ali et al., Therapeutic Potential of Vasopressin Receptor Antagonists, Drugs, vol. 67, No. 6, pp. 847-858, 2007.*
Ashwell, M.A., et al., "The Design, Synthesis and Physico-chemical Properties of a Novel Series of Human Vasopressin $V_2$ Receptor Antagonists", *Wyeth-Ayerst Research*, Princeton, New Jersey, 2000.
Dusza, J. P., et al., "Way-VNA-932: The First Orally Active, Nonpeptide, Vasopressin V2-Receptor Selective Agonist", *Wyeth-Ayerst Research*, Princeton, New Jersey, 2000.
Shumsky, J. S., et al., "Pyridobenzodiazepines: Synthesis and Structure-Activity Relationships of a Novel Class of Orally Active Vasopressin $V_2$ Receptor", *Chemical Sciences Wyeth-Ayerst Research*, Princeton, N.J. 2000.
Shimada, Y., et al., "4,4-Difluoro-5-Methylene-2,3,4,5-Tetrahyro-1H-1-Benzazepine Derivatives: Highly Potent and Selective Antagonist of Arginine Vasopressin V1A Receptor", Japan Pharmaceutical Co., Ltd., Japan, 2000.
Kazumi, K., et al., "7-Chloro-5-hydroxy-1-[2-methyl-4-(2-methylbenzoyl-amino) benzoyl]-2,3,4,5-tetrahydro-1H-1-benzazepine (OPC-41061): A Potent, Orally Active Nonpeptide Arginine Vasopressin $V_2$ Receptor Antagonist", *Bioorganic & Medicinal Chemistry* 7, 1999, pp. 1743-1754, Second Tokushima Institute of New Drug Research, Otsuka Pharmaceutical Co., Ltd., Japan.
Matschisa, A. et al., "Nonpetide Arginine Vasopressin Antagonists for Both $V_{1A}$ and $V_2$ Receptor. Synthesis and Pharmacological Properties of 4'-[5-(Substituted Methylidene)-2,3,4,5-tetrahydro-1H-1-benzoazepine-1-carbonyl]benzanilide and 4'{5-(Substituted Methyl)-2,3-dihydro-1H-1-benzoazepine-1-carbonyl]benzanilide Derivatives", Pharmaceutical Society of Japan 1999, *Institute for Drug Discovery Research*, Yamanouchi Pharmaceutical Co., Ltd., Japan.

(Continued)

*Primary Examiner*—Brenda L Coleman
(74) *Attorney, Agent, or Firm*—Jeremy K. McKown

(57) ABSTRACT

The invention is directed to nonpeptide substituted benzazepines of Formula I, which are useful as vasopressin receptor antagonists for treating conditions associated with vasopressin receptor activity such as those involving increased vascular resistance and cardiac insufficiency, including congestive heart failure, hyponatremia, and hypertension, among others disclosed. Pharmaceutical compositions comprising a compound of Formula I and methods of treating conditions such as hypertension, congestive heart failure, cardiac insufficiency, coronary vasospasm, cardiac ischemia, liver cirrhosis, hyponatremia, renal vasospasm, renal failure, diabetic nephropathy, cerebral edema, cerebral ischemia, stroke, thrombosis, or water retention are also disclosed.

22 Claims, No Drawings

OTHER PUBLICATIONS

Albright D. J., et al., 5-Fluoro-2-methyl-N-[4-(5H-pyrrolo2,1-c-1,4] benzodiazepine-10(11H)-ylcarbonyl)-3-Orally Active Arginine Vasopressin Antagonist with Selectivity for $V_2$ Receptor, *J. Med. Chem.*, 1998, 41, pp. 2442-2444, American Chemical Society.

Ohkawa, T. et al.; "Synthesis and Characterization of Orally Active Nonpeptide Vasopressin V2 Receptor Antagonists". 1999, *Chem. Pharm. Bull.* 47(4) 501-510 Pharm. Society of Japan.

Kondo, K, et al., "Novel Design of Nonpeptide AVP $V_2$ Receptor Agonists: Structural Requirements for an Agonist Having 1-(4-Aminobenzoyl)-2,3,4,5-tetrahydro-1H-1-benzazepine as a Template", *J. Med. Chem.*, 2000, 43, pp. 4388-4397, American Chemical Society.

Yatsu, T., et al "Pharmacological Profile of YM087, a novel nonpeptide dual vasopresin $V_{1A}$ and $V_2$ receptor Antagonists, in dogs", *European Journal of Pharmacology*, 1997, 231, pp. 225-230, Elsevier Science B.V.

Yamamura. Y., et al:,"OPC-41061, a Highly Potent Human Vasopressin $V_2$-Receptor Antagonist: Pharmacological Profile Aquaretic Effect by Single and Multiple Oral Dosing in Rats", *The Journal of Pharmacology and Experimental Therapeutics*, 1998, vol. 287, No. 3, pp. 860-867, Second Tokushima Institute of New Drug Research et al., Japan.

Venkatesan H., et al., Total Synthesis of SR 121463 A, a Highly Potent and Selective Vasopressin V2 Receptor Antagonist, *The Journal of Organic Chemistry*, 2001, vol. 66, No. 11, pp. 3653-3661, American Chemical Society.

Xiang, M. A., "Synthesis and evaluation of nonpeptide substituted spirobenzazepines as potent vasopressin antagonists". *Bioorganic & Medicinal Chem. Lett.*, 2004, vol. 14, 3143-3146.

Xiang, M.A.; "Synthesis and evaluation if spirobenzazephines as potent vasopressin receptor antagonists". *Bioorganic & Medicinal Chem. Lett.*, 2004, vol. 14, 2987-2989.

PCT International Search Report dated May 13, 2005 for PCT/US2004/019460. which relates to U.S. Appl. No. 10/869,746.

Xiang, M. A., et al. Next-Generation Spirobenzazepines: Identification of RWJ-676070 as a Balanced Vasopressin $V_{1a}$/$V_2$ Receptor Antagonist for Human Clinical Studies, Bioorganic & Medical Chemistry Letters, (2007) vol. 17, 6623-6628.

Ashwell, M.A., et al., "The Design, Synthesis and Physico-chemical Properties of a Novel Series of Human Vasopressin $V_2$ Receptor Antagonists", *Wyeth-Ayerst Research*, Princeton, New Jersey, 2000.

Dusza, J. P., et al., "Way-VNA-932: The First Orally Active, Nonpeptide Vasopressin V2-Receptor Selective Agonist", *Wyeth-Ayerst Research*, Princeton, New Jersey, 2000.

Shumsky, J. S., et al., "Pyridobenzodiazepines: Synthesis and Structure-Activity Relationships of a Novel Class of Orally Active, Vasopressin $V_2$ Receptor", *Chemical Sciences Wyeth-Ayerst Research*, Princeton, N.J. 2000.

Shimada, Y., et al., "4,4-Difluoro-5-Methylene-2,3,4,5-Tetrahyro-1H-1-Benzazepine Derivatives: Highly Potent and Selective Antagonist of Arginine Vasopressin V1A Receptor", Japan Pharmaceutical Co., Ltd., Japan. 1997.

Kazumi, K., et al., "7-Chloro-5-hydroxy-1-[2-methyl-4-(2-methylbenzoyl-amino) benzoyl]-2,3,4,5-tetrahydro-1H-1-benzazepine (OPC-41061): A Potent, Orally Active Nonpeptide Arginine Vasopressin $V_2$ Receptor Antagonist", *Bioorganic &* *Medicinal Chemistry* 7, 1999, pp. 1743-1754, Second Tokushima Institute of New Drug Research, Otsuka Pharmaceutical Co., Ltd., Japan.

Matschisa, A. et al., "Nonpetide Arginine Vasopressin Antagonists for Both $V_{1A}$ and $V_2$ Receptor: Synthesis and Pharmacological Properties of 4'-[5-(Substituted Methylidene)-2,3,4,5-tetrahydro-1H-1-benzoazepine-1-carbonyl]benzanilide and 4'-{5-(Substituted Methyl)-2,3-dihydro-1H-1-benzoazepine-1-carbonyllbenzanilide Derivatives", Pharmaceutical Society of Japan 1999, *Institute for Drug Discovery Research*, Yamanouchi Pharmaceutical Co., Ltd., Japan.

Albright D. J., et al., 5-Fluoro-2-methyl-N-[4-(5H-pyrrolo2,1-c-1,4] benzodiazepine-10(11H)-ylcarbonyl)-3-Orally Active Arginine Vasopressin Antagonist with Selectivity for $V_2$ Receptor, *J. Med. Chem.*, 1998, 41, pp. 2442-2444, American Chemical Society.

Ohkawa, T. et al.; "Synthesis and Characterization of Orally Active Nonpeptide Vasopressin V2 Receptor Antagonists". *1999, Chem. Pharm. Bull.* 47(4) 501-510, Pharm. Society of Japan.

Xiang, M. A., "Synthesis and evaluation of nonpeptide substituted spirobenzazepines as potent vasopressin antagonists". *Bioorganic & Medicinal Chem. Lett.*, 2004, vol. 14, 3143-3146.

Kondo, K., et al., "Novel Design of Nonpeptide AVP $V_2$ Receptor Agonists: Structural Requirements for an Agonist Having 1-(4-Aminobenzoyl)-2,3,4,5-tetrahydro-1H-1-benzazepine as a Template", *J. Med. Chem. 2000*, 43, pp. 4388-4397, American Chemical Society.

Yatsu, T., et al., "Pharmacological Profile of YM087, a novel nonpeptide dual vasopresin $V_{1A}$ and $V_2$ receptor Antagonists, in dogs", *European Journal of Pharmacology*, 1997 231, pp. 225-230, Elsevier Science B.V.

Yamamura. Y., et al.,"OPC-41061, a Highly Potent Human Vasopressin $V_2$-Receptor Antagonist: Pharmacological Profile Aquaretic Effect by Single and Multiple Oral Dosing in Rats" *The Journal of Pharmacology and Experimental Therapeutics*, 1998, vol. 287, No. 3, pp. 860-867, Second Tokushima Institute of New Drug Research et al., Japan.

Venkatesan H., et al., Total Synthesis of SR 121463 A, a Highly Potent and Selective Vasopressin V2 Receptor Antagonist, *The Journal of Organic Chemistry*, 2001, vol. 66, No. 11, pp. 3653-3661, American Chemical Society.

Xiang, M.A.; "Synthesis and evaluation if spirobenzazephines as potent vasopressin receptor antagonists". *Bioorganic & Medicinal Chem. Lett.*, 2004, vol. 14, 2987-2989.

Berge et al., "Pharmaceutical Salts.", J. Pharm.Sci., 1977, vol. 66(1), pp. 1-19.

Fujisawa et al., "Therapeutic efficacy of non-peptide ADH antagonist OPC-31260 in SIADH rats.", Kidney Intl., vol. 44, 1993, pp. 19-23.

Liebsch et al., "Septal Vasopressin Modulates Anxiety-related behaviour in rats.", Neuroscience Letters, 1996, vol. 217, pp. 101-104.

Ogawa et al., "Orally Active, Nonpeptide Vasopressin $V_2$ Receptor Antagonists: A Notel Series of 1-[4-(Benzoylamino)benzoyl]-2,3,4,5-tetrahydro-1H-benzazepines and Related Compounds.", J. Med. Chem., 1996 vol. 39, pp. 3547-3555.

Van Zwieten, P.A., "Compensatory mechanisms associated with congestive heart failure as targets for drug treatment.", Progress in Pharmacology and Clinical Pharmacology, 1990, vol. 713, pp. 49-66.

* cited by examiner

SUBSTITUTED SPIROBENZAZEPINES

CROSS-REFERENCE TO RELATED APPLICATION

This application is a continuation of U.S. application Ser. No. 10/869,746, filed on Jun. 16, 2004 now abandoned, which claims the benefit of U.S. Provisional Application Ser. No. 60/479,378 filed Jun. 17, 2003 the contents of which are hereby incorporated by reference.

FIELD OF THE INVENTION

This invention relates to novel nonpeptide substituted spirobenzazepines useful as, for example, vasopressin receptor antagonists.

BACKGROUND OF THE INVENTION

Vasopressin is a nonpeptide hormone that is secreted primarily from the posterior pituitary gland. The hormone effects its actions through the vascular V-1 and renal V-2 receptor subtypes. The functions of vasopressin include contraction of uterine, bladder, and smooth muscle; stimulation of glycogen breakdown in the liver; induction of platelet aggregation; release of corticotropin from the anterior pituitary and stimulation of renal water reabsorption. As a neurotransmitter within the central nervous system (CNS), vasopressin can affect aggressive behavior, sexual behavior, the stress response, social behavior and memory. The V-1a receptor mediates central nervous system effects, contraction of smooth muscle and hepatic glycogenolytic effects of vasopressin, while the V-1b receptor mediates anterior pituitary effects of vasopressin. The V-2 receptor, presumably found only in the kidney, effects the antidiuretic actions of vasopressin via stimulation of adenylate cyclase (Liebsch, G et al *Neurosci.* 1996, 217, 101).

Elevated plasma vasopressin levels appear to play a role in the pathogenesis of congestive heart failure (P. A. Van Zwieten, *Progr. Pharmacol. Clin. Pharmacol.* 1990, 7, 49). As progress toward the treatment of congestive heart failure, nonpeptide vasopressin V-2 receptor antagonists have induced low osmolality aquaresis and decreased peripheral resistance in conscious dogs with congestive heart failure (H. Ogawa, *J. Med. Chem.* 1996, 39, 3547). In certain pathological states, plasma vasopressin levels may be inappropriately elevated for a given osmolality, thereby resulting in renal water retention and hyponatremia. Hyponatremia, associated with edematous conditions (cirrhosis, congestive heart failure, renal failure), can be accompanied by the syndrome of inappropriate secretion of antidiuretic hormone (SIADH). Treatment of SIADH-compromised rats with a vasopressin V-2 antagonist has corrected their existing hyponatremia (G. Fujisawa, *Kidney Int.* 1993, 44(1), 19). Due in part to the contractile actions of vasopressin at its V-1 receptor in the vasculature, vasopressin V-1 antagonists have reduced blood pressure as a potential treatment for hypertension as well. Known vasopressin receptor antagonists have included YM-087 (Yamanouchi); VPA-985, WAY-140288, and CL-385004 (American Home Products); SR-121463 (Sanofi-Synthelabo); and OPC 31260, OPC 41061, and OPC 21268 (Otsuka).

Thus, vasopressin receptor antagonists are useful as therapeutics in the conditions of hypertension, hyponatremia, congestive heart failure/cardiac insufficiency, coronary vasospasm, cardiac ischemia, liver cirrhosis, renal vasospasm, renal failure, diabetic nephropathy, cerebral edema and ischemia, stroke, thrombosis, and water retention. Additional conditions may include nephrotic syndrome, central nervous system injuries, dysmenorrhea, aggression, anxiety and obsessive-compulsive disorders.

SUMMARY OF THE INVENTION

The present invention is directed to compounds represented by the following Formula I:

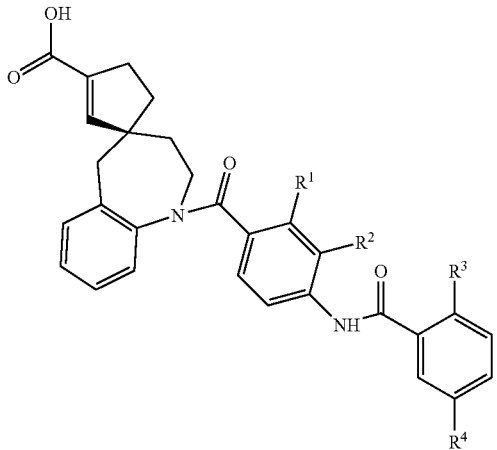

wherein
one of $R^1$ and $R^2$ is H and the other is H, $NR^5R^6$, $C_{1-6}$ alkoxy, hydroxy, or halo; wherein each of $R^5$ and $R^6$ is independently H or $C_{1-3}$ alkyl;
$R^3$ is chloro;
$R^4$ is chloro, fluoro, methoxy, or methyl;
or a pharmaceutically acceptable $C_{1-6}$ ester, $C_{1-6}$ amide, or di($C_{1-6}$ alkyl)amide or salt thereof.

The compounds of the present invention are vasopressin receptor antagonists which are useful, in general, in disease states of inner ear disorders, hypertension, congestive heart failure, cardiac insufficiency, hyponatremia, coronary vasospasm, cardiac ischemia, liver cirrhosis, renal vasospasm, renal failure, diabetic nephropathy, cerebral edema and ischemia, stroke, thrombosis, water retention, aggression, obsessive-compulsive disorders, dysmenorrhea, nephrotic syndrome, and central nervous injuries.

Preferably, the disease state is selected from hypertension, congestive heart failure, cardiac insufficiency, and hyponatremia.

The invention also features a pharmaceutical composition comprising a pharmaceutically acceptable carrier and any of the compounds of Formula I described above, and a pharmaceutical composition made by mixing one or more of the compounds of Formula I and a pharmaceutically acceptable carrier. The invention also features a process for making a pharmaceutical composition comprising mixing any of the compounds described above and a pharmaceutically acceptable carrier.

The invention further provides methods for using a compound or composition of the invention. For example, one embodiment of the invention is a method for treating a condition associated with vasopressin receptor activity, such as a condition mediated by vasopressin antagonism, in a subject in need thereof comprising administering to the subject a therapeutically effective amount of any of the disclosed compounds or the disclosed pharmaceutical compositions.

Another embodiment of the invention is a method of inhibiting the onset or progression of a condition associated with vasopressin receptor activity in the subject, which comprises administering to the subject a prophylactically effective dose of the pharmaceutical composition of a compound of Formula I.

An additional illustration of the invention is a method of treating a condition selected from hypertension, congestive heart failure, cardiac insufficiency, hyponatremia, coronary vasospasm, cardiac ischemia, liver cirrhosis, renal vasospasm, renal failure, diabetic nephropathy, cerebral edema, cerebral ischemia, stroke, thrombosis, and water retention in a subject in need thereof, such method comprising administering to the subject a therapeutically effective amount of any of the compounds or pharmaceutical compositions described above. Preferably, the therapeutically effective amount of the compound administered for treating any of these conditions is about 0.05 to 1 g per day.

Other embodiments and features of the invention are disclosed in the following detailed description, examples, and the appended claims.

DETAILED DESCRIPTION OF THE INVENTION

The present invention provides nonpeptide substituted spirobenzazepine compounds which are useful as antagonists of vasopressin receptors. Particularly, these substituted spirobenzazepine compounds inhibit the binding of vasopressin to V-1a, V-1b, and/or V-2 receptors, and preferably V-1a, and V-2 receptors. The compounds of this invention also show functional activity by their ability to inhibit intracellular calcium mobilization and cAMP accumulation induced by arginine vasopressin (AVP) in transfected HEK-293 cells expressing human V-1a and V-2 receptors respectively.

The nonpeptide substituted spirobenzazepine compounds of the present invention are vasopressin receptor antagonists. In a preferred embodiment, the compounds are orally active. In another preferred embodiment, the compounds have the ability to block vasopressin binding to V-1a and V-2 to a greater extent than to V-1b. As demonstrated by the results of the pharmacological studies described hereinafter, the compounds show the ability to block vasopressin binding to recombinant V-1a, and/or V-2, and therefore are useful as therapeutics in or prophylactics against conditions such as aggression, obsessive-compulsive disorders, hypertension, dysmenorrhea, hyponatremia, congestive heart failure/cardiac insufficiency, coronary vasospasm, cardiac ischemia, liver cirrhosis, renal vasospasm, renal failure, edema, ischemia, stroke, thrombosis, water retention, nephrotic syndrome, anxiety and central nervous injuries.

A. TERMS

The following terms are defined below and by their usage throughout this disclosure.

"Alkyl" includes optionally substituted straight chain, branched, or cyclic hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl includes cycloalkyl, such as cyclopropyl, cyclobutyl, cyclopentyl, and cyclohexyl. For example, $C_3$ alkyl includes n-propyl, isopropyl, and cyclopropyl; $C_4$ alkyl includes n-butyl, isobutyl, t-butyl, cyclobutyl, cyclopropylmethyl, and methylcyclopropyl.

"Alkoxy" includes an optionally substituted straight chain, branched, or cyclic alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, SO and $SO_2$.

"Halo" or "halogen" includes fluoro, chloro, bromo, and iodo, and preferably fluoro or chloro. As a substituent on an alkyl group, with one or more halo atoms, halo can provide mono-, di-, and tri-substituted groups such as trifluoromethyl, trifluoromethoxy, trifluoromethylthio, difluoromethoxy, or fluoromethylthio.

"Pharmaceutically acceptable salts, esters, and amides" include carboxylate salts, amino acid addition salts, esters, and amides which are within a reasonable benefit/risk ratio, pharmacologically effective and suitable for contact with the tissues of patients without undue toxicity, irritation, or allergic response. These salts, esters, and amides may be, for example, $C_{1-8}$ alkyl, $C_{3-8}$ cycloalkyl, aryl, $C_{2-10}$ heteroaryl, or $C_{2-10}$ non-aromatic heterocyclic salts, esters, and amides. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl and ethyl esters. Other examples include $C_{1-6}$ alkyl, $C_{1-5}$ alkyl, $C_{1-4}$ alkyl, or $C_{1-3}$ alkyl esters or amides. With respect to dialkyl amides, each alkyl group is selected independently.

Representative salts include hydrobromide, hydrochloride, hydroiodide, perchlorate, sulfate, bisulfate, nitrate, acetate, oxalate, valerate, oleate, palmitate, stearate, laurate, borate, boronate, benzoate, lactate, phosphate, tosylate, citrate, maleate, fumarate, succinate, tartrate, naphthylate, mesylate, glucoheptonate, lactiobionate, methanesulfonate, pamoate, salicylate, saccharinnic and laurylsulfonate. These may include alkali metal and alkali earth cations such as sodium, potassium, calcium, and magnesium, zinc, as well as non-toxic ammonium, quaternary ammonium, and amine cations such as tetramethyl ammonium, methylamine, trimethylamine, and ethylamine. See example, S. M. Berge, et al., "Pharmaceutical Salts," J. Pharm. Sci., 1977, 66: 1-19; "Handbook of Pharmaceutical Salts—Properties, Selection, and Use" P. Heinrich Stahl, Camille G. Wermuth—Eds., Wiley-VCH Publishers, Zurich, Switzerland which are incorporated herein by reference.

Representative pharmaceutically acceptable amides of the invention include those derived from ammonia, primary $C_{1-6}$ alkyl amines and secondary di($C_{1-6}$ alkyl)amines. Dialkylamides have two alkyl groups that may be independently selected (e.g., methylpropylamide). Secondary amines include 5- or 6-membered heterocyclic or heteroaromatic ring moieties such as morpholinyl containing at least one nitrogen atom and optionally between 1 and 2 additional heteroatoms. Preferred amides are derived from ammonia, $C_{1-3}$ alkyl primary amines, and di($C_{1-2}$ alkyl)amines.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient or subject is a human.

"Composition" includes a product comprising the specified ingredients in the specified amounts as well as any product that results from combinations of the specified ingredients in the specified amounts.

"Therapeutically effective amount" or "effective amount" (or "prophylactically effect amount") means that amount of active compound or pharmaceutical agent that elicits the biological or medicinal response in a tissue system, animal or human that is being sought by a researcher, veterinarian, medical doctor or other clinician, which includes alleviation (or prevention, or delay or inhibition of onset) of the symptoms of the condition or disorder being treated.

"Prophylactically effect amount" means that amount of active compound or pharmaceutical agent that elicits the biological or medicinal response in a tissue system, animal or human that is being sought by a researcher, veterinarian, medical doctor or other clinician, which includes prevention, or delay or inhibition of onset, of the symptoms of the condition or disorder being treated.

Concerning the various radicals in this disclosure and in the claims, three general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent).

Second, radicals or structure fragments as defined herein are understood to include substituted radicals or structure fragments. Hydrocarbyls include monovalent radicals containing carbon and hydrogen such as alkyl, alkenyl, alkynyl, cycloalkyl, and cycloalkenyl (whether aromatic or unsaturated), as well as corresponding divalent (or multi-valent) radicals such as alkylene, alkenylene, phenylene, and so on. Heterocarbyls include monovalent and divalent (or multivalent) radicals containing carbon, optionally hydrogen, and at least one heteroatom. Examples of monovalent heterocarbyls include acyl, acyloxy, alkoxyacyl, heterocyclyl, heteroaryl, aroyl, benzoyl, dialkylamino, hydroxyalkyl, and so on. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, trifluoromethyl, and 3-iodocyclopentyl), hydroxyalkyl (such as hydroxymethyl, hydroxyethyl, 2-hydroxypropyl, aminoalkyl (such as aminomethyl, 2-aminoethyl, 3-aminopropyl, and 2-aminopropyl), nitroalkyl, alkylalkyl, and so on. A di($C_{1-6}$ alkyl)amino group includes independently selected alkyl groups, to form, for example, methylpropylamino and isopropylmethylamino, in addition dialkylamino groups having two of the same alkyl group such as dimethyl amino or diethylamino.

According to one embodiment, hydrogens on the rings in the formula I that are not assigned (e.g., are not $R^1$, $R^2$, $R^3$, or $R^4$) are not substituted.

Third, only stable compounds are intended.

B. COMPOUNDS

The present invention features substituted benzazepines of Formula I in the Summary of the Invention section having pharmaceutical activity, such as dual V1a/V2 antagonists. Examples of compounds include those wherein: (a) $R^2$ is amino; (b) $R^1$ or $R^2$ (or preferably $R^2$) is a $C_{1-6}$ alkoxy, or a $C_{1-5}$ alkoxy, or a $C_{1-4}$ alkoxy or a $C_{1-3}$ alkoxy; (c) $R^1$ or, preferably, $R^2$ is methoxy, ethoxy, propoxy, isopropoxy, cyclopropoxy, butoxy, isobutoxy, cyclobutoxy, cyclopropylmethoxy, or t-butoxy; (d) $R^2$ is methoxy or ethoxy; (e) $R^4$ is fluoro, chloro, or methyl; (f) $R^4$ is fluoro or chloro; (g) $R^4$ is fluoro; (h) $R^2$ is methoxy, ethoxy, or isopropoxy and $R^4$ is fluoro, chloro, or methyl; (i) $R^2$ is methoxy or ethoxy and $R^4$ is fluoro, chloro, or methyl; (j) $R^2$ is methoxy or ethoxy and $R^4$ is fluoro or chloro; (k) $R^2$ is methoxy or ethoxy and $R^4$ is fluoro or methyl; (l) $R^2$ is methoxy or ethoxy and $R^4$ is fluoro; (m) the compound is a compound of formula I or a pharmaceutically acceptable salt or ester thereof; (n) the compound is a compound of formula I, or a pharmaceutically acceptable salt thereof; (o) the compounds of formula I are not further substituted; (p) any alkyl or alkylene group of the compound may be substituted with halo, methyl, methoxy, hydroxy, amino, or cyano; (q) $R^2$ is H, hydroxy, amino, $C_{1-4}$ alkoxy, or halo; (r) $R^1$ is H; (s) where (q) and (r) apply; (t) where substitutions occur only on the carboxyl; (u) only on $R^2$ and $R^4$; (v) only on the 5-membered spiro ring; (x) where (t) and (u) apply; (y) where (t), (u), and (v) apply; (z) $R^1$ or $R^2$ (or preferably $R^2$) is amino, methylamino, ethylamino, n-propyl amino, cyclopropylamino, or isopropylamino; (aa) $R^1$ or, preferably, $R^2$ is dimethyl amino, methyl ethylamino, methyl (n- or iso-propyl)amino, diethylamino, ethyl (iso- or n-propyl)amino, or dipropyl amino (bb) $R^2$ is methylamino, dimethylamino, or ethylamino; (cc) or combinations of two, three, or four of any of the above (a) through (bb).

Compounds of the invention can further include those wherein $R^4$ can also be H, or wherein $R^3$ can also be fluoro, bromo, methyl, amino, methylamino, dimethylamino, halomethyl, hydroxy, methylthio ($CH_3S-$), cyclopropyl, or methoxy.

Examples of preferred compounds include:

(R)-4-(2-Chloro-5-fluorobenzoyl-3-methoxy-4-aminobenzoyl)-4-aza-3'-(carboxy)-[6,4]-spiro-[5,6]-benzoundec-2'-ene (R)-4-(2-Chloro-5-fluorobenzoyl-3-ethoxy-4-aminobenzoyl)-4-aza-3'-(carboxy)-[6,4]-spiro-[5,6]-benzoundec-2'-ene (R)-4-(2-Chloro-5-fluorobenzoyl-3-isopropoxy-4-aminobenzoyl)-4-aza-3'-(carboxy)-[6,4]-spiro-[5,6]-benzoundec-2'-ene (R)-4-(2-Chloro-5-fluorobenzoyl-3-hydroxy-4-aminobenzoyl)-4-aza-3'-(carboxy)-[6,4]-spiro-[5,6]-benzoundec-2'-ene (R)-4-(2-Chloro-5-fluorobenzoyl-4-aminobenzoyl)-4-aza-3'-(carboxy)-[6,4]-spiro-[5,6]-benzoundec-2'-ene (R)-4-(2-Chloro-5-fluorobenzoyl-3-amino-4-aminobenzoyl)-4-aza-3'-(carboxy)-[6,4]-spiro-[5,6]-benzoundec-2'-ene (R)-4-(2-Chloro-5-fluorobenzoyl-3-chloro-4-aminobenzoyl)-4-aza-3'-(carboxy)-[6,4]-spiro-[5,6]-benzoundec-2'-ene (R)-4-(2-Chloro-5-fluorobenzoyl-2-chloro-4-aminobenzoyl)-4-aza-3'-(carboxy)-[6,4]-spiro-[5,6]-benzoundec-2'-ene (R)-4-(2-Chloro-5-fluorobenzoyl-2-amino-4-aminobenzoyl)-4-aza-3'-(carboxy)-[6,4]-spiro-[5,6]-benzoundec-2'-ene (R)-4-(2-Chloro-5-fluorobenzoyl-2-hydroxy-4-aminobenzoyl)-4-aza-3'-(carboxy)-[6,4]-spiro-[5,6]-benzoundec-2'-ene (R)-4-(2-Chloro-5-fluorobenzoyl-2-methoxy-4-aminobenzoyl)-4-aza-3'-(carboxy)-[6,4]-spiro-[5,6]-benzoundec-2'-ene (R)-4-(2-Chloro-5-methylbenzoyl-3-methoxy-4-aminobenzoyl)-4-aza-3'-(carboxy)-[6,4]-spiro-[5,6]-benzoundec-2'-ene (R)-4-(2-Chloro-5-methylbenzoyl-3-hydroxy-4-aminobenzoyl)-4-aza-3'-(carboxy)-[6,4]-spiro-[5,6]-benzoundec-2'-ene (R)-4-(2-Chloro-5-methylbenzoyl-4-aminobenzoyl)-4-aza-3'-(carboxy)-[6,4]-spiro-[5,6]-benzoundec-2'-ene (R)-4-(2-Chloro-5-methylbenzoyl-3-amino-4-aminobenzoyl)-4-aza-3'-(carboxy)-[6,4]-spiro-[5,6]-benzoundec-2'-ene (R)-4-(2-Chloro-5-methylbenzoyl-3-chloro-4-aminobenzoyl)-4-aza-3'-(carboxy)-[6,4]-spiro-[5,6]-benzoundec-2'-ene (R)-4-(2-Chloro-5-methoxybenzoyl-3-methoxy-4-aminobenzoyl)-4-aza-3'-(carboxy)-[6,4]-spiro-[5,6]-benzoundec-2'-ene (R)-4-(2-Chloro-5-methoxybenzoyl-3-hydroxy-4-aminobenzoyl)-4-aza-3'-(carboxy)-[6,4]-spiro-[5,6]-benzoundec-2'-ene (R)-4-(2-Chloro-5-methoxybenzoyl-4-aminobenzoyl)-4-aza-3'-(carboxy)-[6,4]-spiro-[5,6]-benzoundec-2'-ene (R)-4-(2-Chloro-5-methoxybenzoyl-3-amino-4-aminobenzoyl)-4-aza-3'-(carboxy)-[6,4]-spiro-[5,6]-benzoundec-2'-ene (R)-4-(2-Chloro-5-methoxybenzoyl-3-chloro-4-aminobenzoyl)-4-aza-3'-(carboxy)-[6,4]-spiro-[5,6]-benzoundec-2'-ene (R)-4-(2,5-Dichlorobenzoyl-3-methoxy-4-aminobenzoyl)-4-aza-3'-(carboxy)-[6,4]-spiro-[5,6]-benzoundec-2'-ene (R)-4-(2,5-Dichlorobenzoyl-3-hydroxy-4-aminobenzoyl)-4-aza-3'-(carboxy)-[6,4]-spiro-[5,6]-benzoundec-2'-ene (R)-4-(2,5-Dichlorobenzoyl-4-aminobenzoyl)-4-aza-3'-(carboxy)-[6,4]-spiro-[5,6]-benzoundec-2'-ene and (R)-4-(2,5-Dichlorobenzoyl-3-amino-4-aminobenzoyl)-4-aza-3'-(carboxy)-[6,4]-spiro-[5,6]-benzoundec-2'-ene (R)-4-(2,5-Dichlorobenzoyl-3-chloro-4-aminobenzoyl)-4-aza-3'-(carboxy)-[6,4]-spiro-[5,6]-benzoundec-2'-ene More preferably, the invention features a compound selected from the target compounds of Example 6 and Example 7; or the compound is the target compound of Example 7; or most preferably, the compound of the invention is the target compound of Example 6.

The invention features, among other things, the discovery that a terminal 2-chlorophenyl with a further substitution at the 5 position appears to be especially advantageous for dual V-1a/V-2 activity, as compared, for example, to a monosubstituted 2-chlorophenyl, or a 2-methyl, 5-fluoro-substituted phenyl.

Preferably the compound is selective, with good bioavailability and low hepatobiliary toxicity.

The invention also features the discovery that the spiro-ring preferably has an (R) configuration, as required by Formula I.

Where the compounds according to this invention have at least one stereogenic center, they may accordingly exist as enantiomers. Where the compounds possess two or more stereogenic centers, they may additionally exist as diastereomers. It is to be understood that all such isomers and mixtures thereof are encompassed within the scope of the present invention. However, Formula I specifies the geometry of the spiro carbon (R) and only (R) is contemplated for the preferred embodiment of the invention.

Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms. Related compounds also include compounds of the invention that have been modified to be detectable, e.g., isotopically labelled with $^{18}F$ for use as a probe in positron emission tomography (PET) or single-photon emission computed tomography (SPECT).

The invention also includes disclosed compounds having one or more functional groups (e.g., hydroxyl, amino, or carboxyl) masked by a protecting group. See, e.g., Greene and Wuts, *Protective Groups in Organic Synthesis*, $3^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyloxymethyl, methylthiomethyl, t-butylthiomethyl, benzyloxymethyl, p-methoxybenzyloxymethyl, (4-methoxyphenoxy)methyl, t-butoxymethyl.

Substituted Ethyl Ethers

Examples of substituted ethyl ethers include 1-ethoxyethyl, 1-methyl-1-methoxyethyl, 1-methyl-1-benzyloxyethyl, 2,2,2-trichloroethyl, t-butyl, allyl, p-chlorophenyl, p-methoxyphenyl, and benzyl.

Substituted Benzyl Ethers

Examples of substituted benzyl ethers include p-methoxybenzyl, 3,4-dimethoxybenzyl, p-halobenzyl, 2,6-dichlorobenzyl, p-cyanobenzyl, p-phenylbenzyl, diphenylmethyl.

Esters

In addition to ethers, a hydroxyl group may be protected as an ester. Examples of esters include formate, benzoylformate, acetate, trichloroacetate, trifluoroacetate, methoxyacetate, phenoxyacetate, p-chlorophenoxyacetate, benzoate.

Sulfonates

Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, and 4-methoxyphenacyl.

Substituted Ethyl

Examples of substituted ethyl carbamates include 2,2,2-trichloroethyl, 2-phenylethyl, t-butyl, vinyl, allyl, 1-isopropylallyl, benzyl, p-methoxybenzyl, p-nitrobenzyl, p-bromobenzyl, p-chlorobenzyl, 2,4-dichlorobenzyl and diphenylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Amides

Examples of amides include N-formyl, N-acetyl, N-trichloroacetyl, N-trifluoroacetyl, N-phenylacetyl, N-3-phenylpropionyl, N-picolinoyl, N-3-pyridylcarboxamide, N-benzoyl, N-p-phenylbenzoyl, and phthaloyl.

Protection for the Carbonyl Group

Cyclic Acetals and Ketals

Examples of cyclic acetals and ketals include 1,3-dioxanes and 5-methylene-1,3-dioxane.

Protection for the Carboxyl Group

Esters

Substituted Methyl Esters

Examples of substituted methyl esters include 9-fluorenylmethyl, methoxymethyl, methylthiomethyl, methoxyethoxymethyl, 2-(trimethylsilyl)ethoxymethyl, benzyloxymethyl, phenacyl, p-bromophenacyl, α-methylphenacyl, and p-methoxyphenacyl. Examples of esters also include straight chain or branched alkyl esters such as tert-butyl, ethyl, propyl, isopropyl, and butyl.

Substituted Benzyl Esters

Examples of substituted benzyl esters include triphenylmethyl, diphenylmethyl, 9-anthrylmethyl, 2,4,6-trimethylbenzyl, p-bromobenzyl, o-nitrobenzyl, p-nitrobenzyl, p-methoxybenzyl, 2,6-dimethoxybenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

C. SYNTHETIC METHODS

The invention provides methods of making the disclosed compounds according to traditional organic synthetic methods as well as matrix or combinatorial synthetic methods. Schemes 1-3 describe suggested synthetic routes. Using these Schemes, the guidelines below, and the examples, a person of skill in the art may develop analogous or similar methods for a given compound that are within the invention. General guidance regarding synthesis is provided in the next section; specific examples with detailed experimental protocols are provided in Section E Examples. Background information may also be found in WO 02/02531 A1, published on Jan. 10, 2002, and incorporated herein by reference.

One skilled in the art will recognize that synthesis of the compounds of the present invention may be facilitated by purchasing an intermediate or protected intermediate compounds described in any of the schemes disclosed herein. One skilled in the art will further recognize that during any of the processes for preparation of the compounds in the present invention, it may be necessary and/or desirable to protect sensitive or reactive groups on any of the molecules concerned. This may be achieved by means of conventional protecting groups, such as those described in "Protective Groups in Organic Synthesis", John Wiley & Sons, 1991. These protecting groups may be removed at a convenient stage using methods known from the art.

Examples of the described synthetic routes include Synthetic Examples 1 through 16. Compounds analogous to the target compounds of these examples can be, and in many cases, have been, made according to similar routes. The disclosed compounds are useful in basic research and as pharmaceutical agents as described in the next section.

The preparation of compound 7 was based on chemistry elucidated in WO 02/02531 A1 and is briefly described as follows. 3-Benzyl-3-formylmethylcyclohexene (commercially available or prepared by following Scheme 1 in U.S. Pat. No. 5,753,715) was oxidized to the corresponding acid. Intramolecular cyclization of the acid provided 3-oxo-[5,5]-spiro-[4,5]-benzoundec-2'-ene. Beckmann rearrangement of the ketone via oxime provided the regioisomeric lactams which were separated by column chromatography to provide 4-aza-3-oxo-[6,5]-spiro-[5,6]-benzoundec-2'-ene. The lactam was reduced to provide the analogous benzazepine. The benzazepine may be protected as the tosylate using tosyl chloride and an acid scavenger such as pyridine or triethylamine in solvent such as dichloromethane or dichloroethane. Ozonolysis can provide 3'-formylspirobenzazepine. Oxidation of the formyl group to the carboxylic acid by treatment with known oxidizing agents such as pyridinium dichromate in dimethylformamide is followed by the removal of the tosyl group by treatment with mineral acid such as hydrochloric or hydrobromic acids. Selective crystallization of camphor sulphonic acid salt can provide (R)-spirobenzazepinecarboxylic acid that may then be converted in Example 1 to the corresponding ethyl ester via Fischer esterification.

The compounds of this invention where $R^1$ or $R^2$ is H, halo, or alkoxy can be made by the chemistry shown in Scheme 1. A carboxylic acid of the general formula 1 can be purchased or synthesized by methods described in the literature, then protected by conversion to an ester of the general formula 2 by treatment with, for instance, an alkylating agent such as dimethyl sulfate and a base such as potassium carbonate in a solvent such as acetone at a temperature between ambient and reflux. Alternatively the ester of the general formula 2 can be synthesized with methanol and a mineral acid such as hydrochloric or sulfuric acid at temperatures ranging from ambient to approximately 60° C. The nitro group in a compound of the general formula 2 can be reduced under the appropriate conditions to the corresponding amine of the general formula 3, with conditions such as catalytic hydrogenation in a solvent such as ethyl acetate, methanol, or ethanol, a catalyst such as palladium on charcoal, and hydrogen gas under 1 to 20 atmospheres of pressure, at temperatures ranging from ambient to approximately 60° C. The amine of the general formula 3 is converted to the corresponding amide of the general formula 5 with an appropriately substituted benzoyl chloride of the general formula 4 and an organic base such as triethylamine in a solvent such as dichloromethane or dichloroethane at temperatures ranging from ambient to approximately 60° C. The benzoyl chloride of the general formula 4 can be purchased or synthesized by literature methods as the acid chloride, or as the corresponding carboxylic acid, then converted to the acid chloride by treatment with a reagent such as thionyl chloride or oxalyl chloride either neat or in a solvent such as dichloromethane or dichloroethane, at temperatures ranging from ambient to approximately 60° C. The ester of general formula 5 can be converted to the acid chloride of the general formula 6 in two steps. First, the ester can be saponified to the carboxylic acid with a base such as lithium hydroxide, sodium hydroxide, or potassium hydroxide in water and a cosolvent such as tetrahydrofuran, dioxane, ethanol, or some combination of solvents, at temperatures ranging from ambient to approximately 80° C. Second, the carboxylic acid is converted to an acid chloride of the general formula 6 by treatment with a reagent such as thionyl chloride or oxalyl chloride either neat or in a solvent such as dichloromethane or dichloroethane, at temperatures ranging from ambient to approximately 60° C. The acid chloride obtained is treated with compound 7 in a mild organic base such as triethylamine in a solvent such as dichloromethane or dichloroethane at temperatures ranging from ambient to approximately 60° C., to yield a compound of the general formula 8. Products of the general formula 9a are obtained from compounds of the general formula 8 by saponification with a base such as lithium hydroxide, sodium hydroxide, or potassium hydroxide in water and an appropriate cosolvent such as tetrahydrofuran, dioxane, ethanol, or some combination of solvents, at temperatures ranging from ambient to approximately 80° C. Aqueous workup with a mineral acid such as hydrochloric acid provides the final product of the general formula 9a.

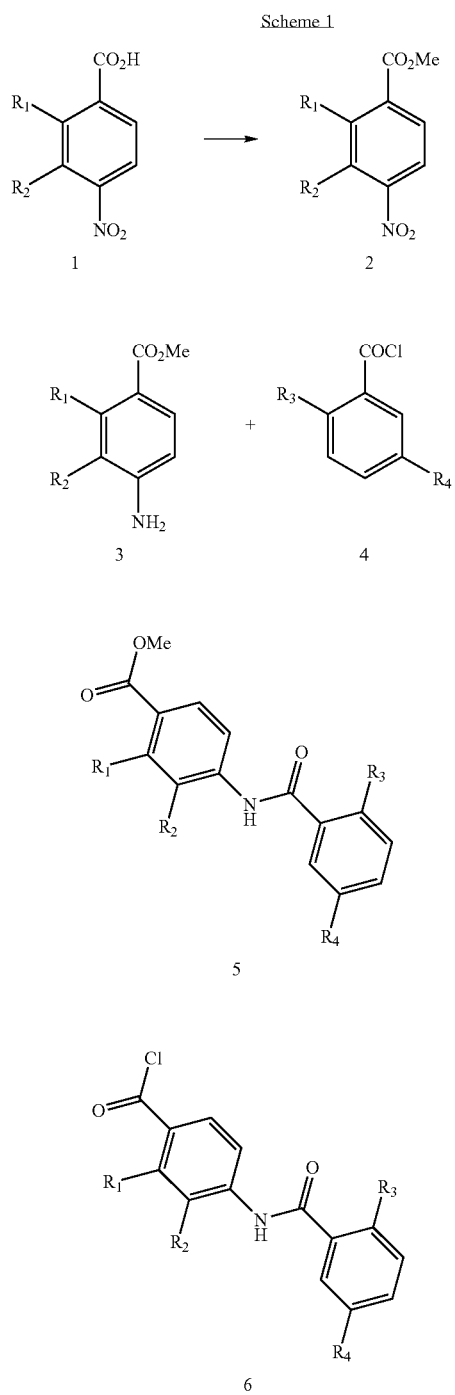

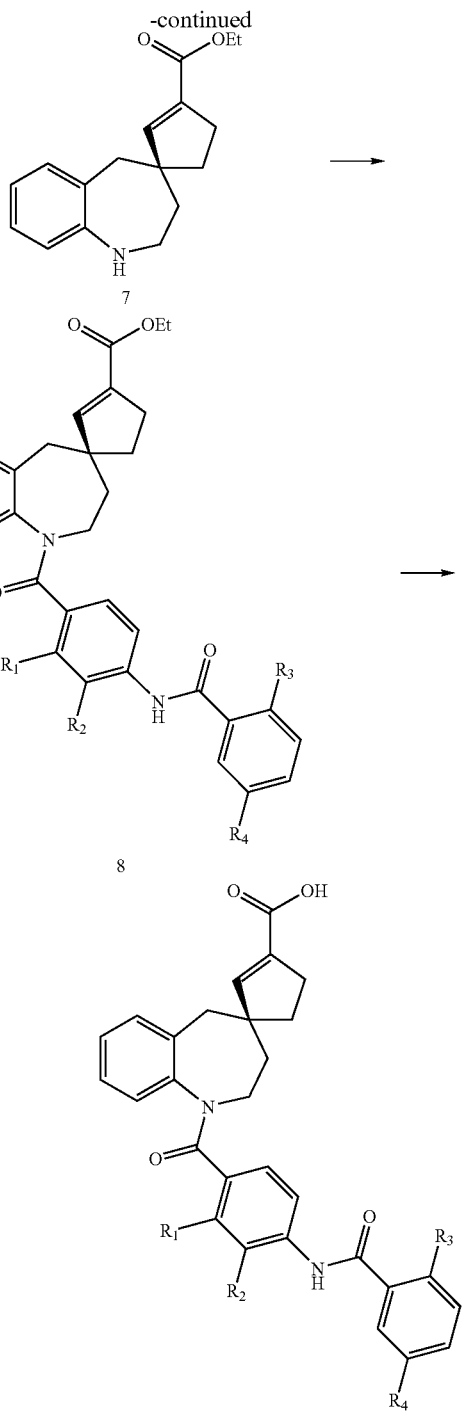

The compounds of this invention where $R^1$ or $R^2$ is H, halo, or alkoxy can also be made by the chemistry shown in Scheme 2. A carboxylic acid of the general formula 1 can be purchased or synthesized by methods described in the literature, then converted to the corresponding acid chloride of the general formula 10 by treatment with a reagent such as thionyl chloride or oxalyl chloride either neat or in a solvent such as dichloromethane or dichloroethane, at temperatures ranging from ambient to approximately 60° C. The compound of the general formula 10 can be treated with compound 7 and an organic base such as triethylamine in a solvent such as dichloromethane or dichloroethane at temperatures ranging from ambient to approximately 60° C., to yield a compound of the general formula 11. The nitro group in the compounds of the general formula 11 can be reduced to an amine of the general formula 12, with a reagents such as tin (II) chloride in an alcoholic solvent, such as methanol, ethanol, propanol and the like, with the caveat that when $R^2$ is an alkoxide, the reaction product may be a mixture of the original alkoxide and the alkoxide from the alcoholic solvent. A compound of the general formula 12 can be converted to the product of the general formula 9a in two steps. First, the amine can be converted to the corresponding amide by treatment with an acid chloride of the general formula 4 (from the description of Scheme 1) and an organic base such as triethylamine in a solvent such as dichloromethane or dichloroethane at temperatures ranging from ambient to approximately 60° C. The intermediate formed can be treated with a base, such as lithium hydroxide, sodium hydroxide, or potassium hydroxide in water and an appropriate cosolvent such as tetrahydrofuran, dioxane, ethanol, or some combination of solvents, at temperatures ranging from ambient to approximately 80° C. Aqueous workup with a mineral acid such as hydrochloric acid provides the final product of the general formula 9a.

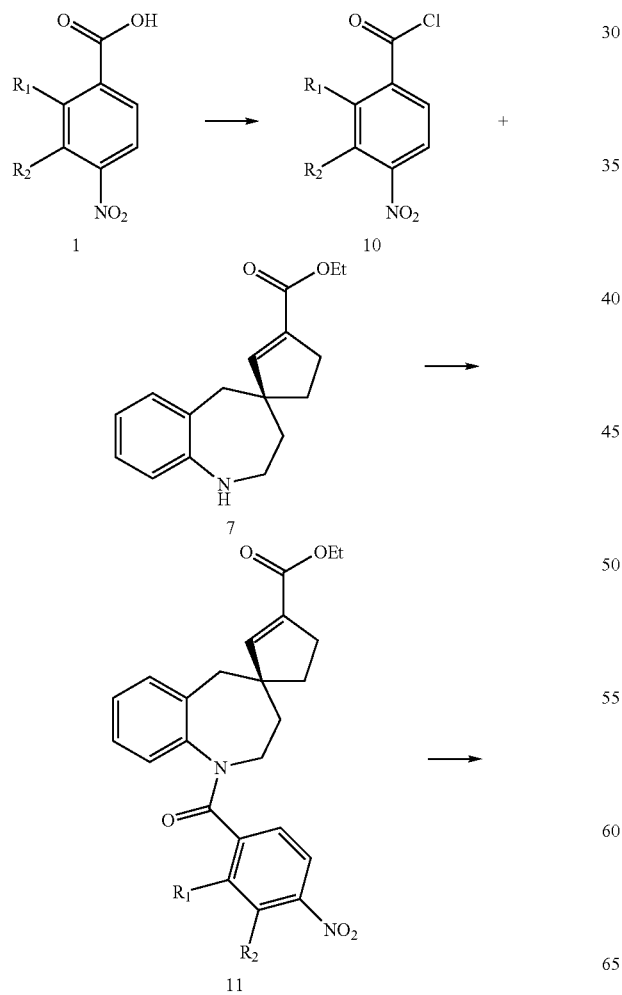

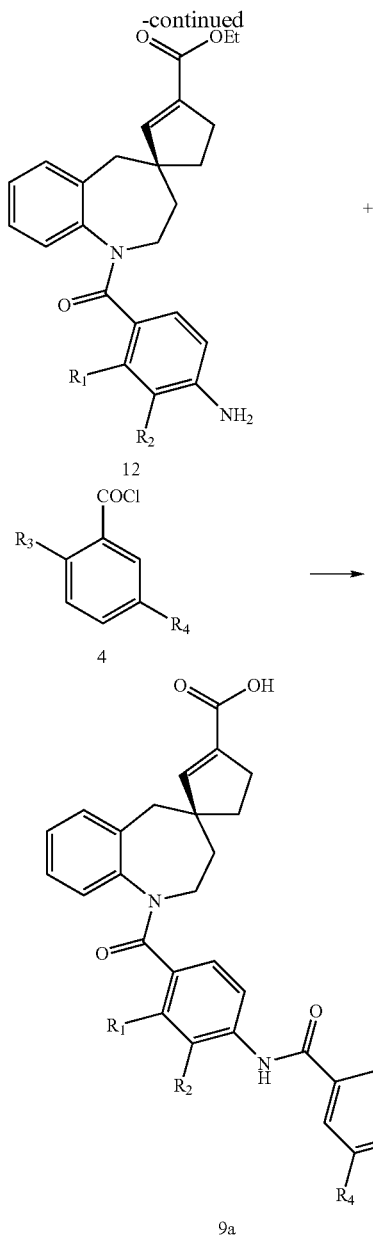

The compounds of this invention where $R^1$ or $R^2$ are hydroxy could be made by the chemistry outlined in Scheme 3. An acid of the general formula 13 could be treated with an acid chloride of the general formula 4 (from the description in Scheme 1) and an organic base such as triethylamine in a solvent such as dichloromethane or dichloroethane at temperatures ranging from ambient to approximately 60° C., to yield a compound of the general formula 14. A compound of the general formula 15 could be obtained by treatment with a reagent such as thionyl chloride or oxalyl chloride either neat or in a solvent such as dichloromethane or dichloroethane, at temperatures ranging from ambient to approximately 60° C. A compound of the general formula 15 could be treated with compound 7 and an organic base such as triethylamine in a solvent such as dichloromethane or dichloroethane at temperatures ranging from ambient to approximately 60° C., to yield a compound of the general formula 16. Products of the general formula 9b could be obtained from compounds of the general formula 16 by saponification with a base such as lithium hydroxide, sodium hydroxide, or potassium hydroxide in water and an appropriate cosolvent such as tetrahydrofuran, dioxane, ethanol, or some combination of solvents, at temperatures ranging from ambient to approximately 80° C. Aqueous workup with a mineral acid such as hydrochloric acid would provide the final product of the general formula 9b.

Scheme 3

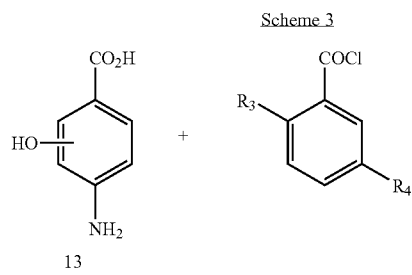

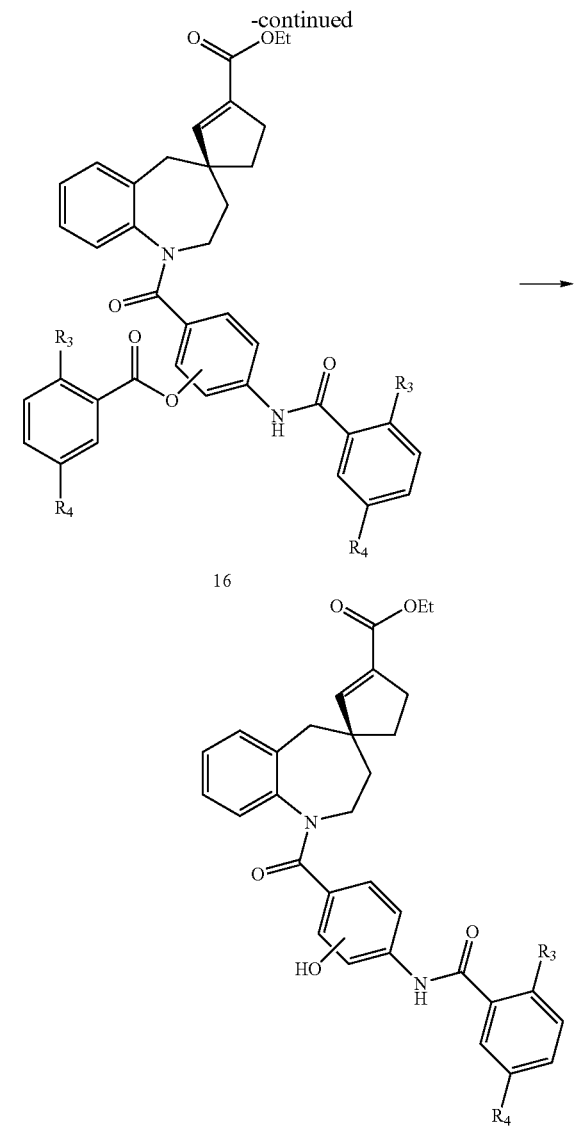

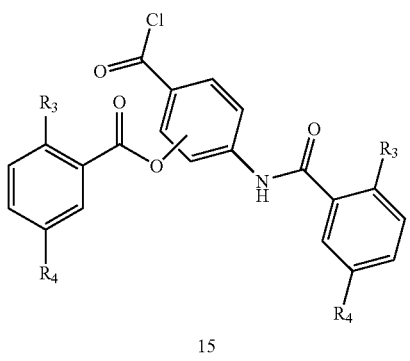

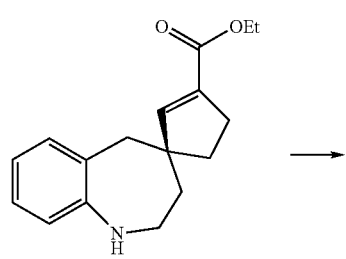

The compounds of this invention where $R^1$ or $R^2$ is amino or substituted amino could be made by the chemistry outlined in Scheme 4. Compounds of the general formula 17 have been reported in the literature and could be converted to compounds of the general formula 18 by treatment with methanol and a catalytic amount of a mineral acid such as sulfuric acid or hydrochloric acid at temperatures ranging from ambient to approximately 60° C. Compounds of the general formula 19 could then be obtained by treatment with 50-100% aqueous hydrazine at temperatures ranging from ambient to approximately 80° C. Compounds of the general formula 19 could then be converted to compounds of the general formula 20 with a reagent such as $(BOC)_2O$ at ambient temperature. Reduction to compounds of the general formula 21 could be achieved by hydrogenation with a catalyst such as palladium on charcoal and hydrogen gas at pressures from 1 to 20 atmospheres in a solvent such as methanol, ethanol, ethyl acetate and the like at temperatures ranging from ambient to approximately 50° C. Compounds of the general formula 21 could be acylated with compounds of the general formula 4 (from the description in Scheme 1) and an organic base such as triethylamine in a solvent such as dichloromethane or dichloroethane at temperatures ranging from ambient to approximately 60° C., to yield a compound of the general formula 22. Saponification to compounds of the general formula 23 could be achieved with a base such as lithium hydroxide, sodium hydroxide, or potassium hydroxide in water and an appropriate cosolvent such as tetrahydrofuran, dioxane, ethanol, or some combination of solvents, at temperatures ranging from ambient to approximately 80° C. Coupling of compounds of the general formula 23 with compound 7 to provide compounds of the general formula 24 could be carried out with a carbodiimide coupling reagent such as DCC or EDC in a solvent such as dichloromethane, dichloroethane, or benzene at temperatures ranging from ambient to 40° C. Compounds of the general formula 25 where $R^5$ and $R^6$ are H could be obtained from compounds of the general formula 24 by treatment with a mineral acid such as hydrochloric acid or sulfuric acid in a solvent methanol, ethanol, ethyl acetate and the like at temperatures ranging from ambient to approximately 40° C. Compounds of the general formula 25 where $R^5$ and $R^6$ are methyl, ethyl, or propyl could be obtained by treatment of compounds of the general formula 24 as above followed by reductive amination under conditions that favor monoalkylation or dialkylation, with formaldehyde, acetaldehyde, or propionaldehyde, then a reducing agent such as sodium cyanoborohydride in a solvent such as methanol, ethanol, tetrahydrofuran, dioxane, and the like at temperatures from 0° C. to approximately 40° C. Products of the general formula 9c could be obtained from compounds of the general formula 25 by saponification with a base such as lithium hydroxide, sodium hydroxide, or potassium hydroxide in water and an appropriate cosolvent such as tetrahydrofuran, dioxane, ethanol, or some combination of solvents, at temperatures ranging from ambient to approximately 80° C. Aqueous workup with a mineral acid such as hydrochloric acid would provide the final product of the general formula 9c.

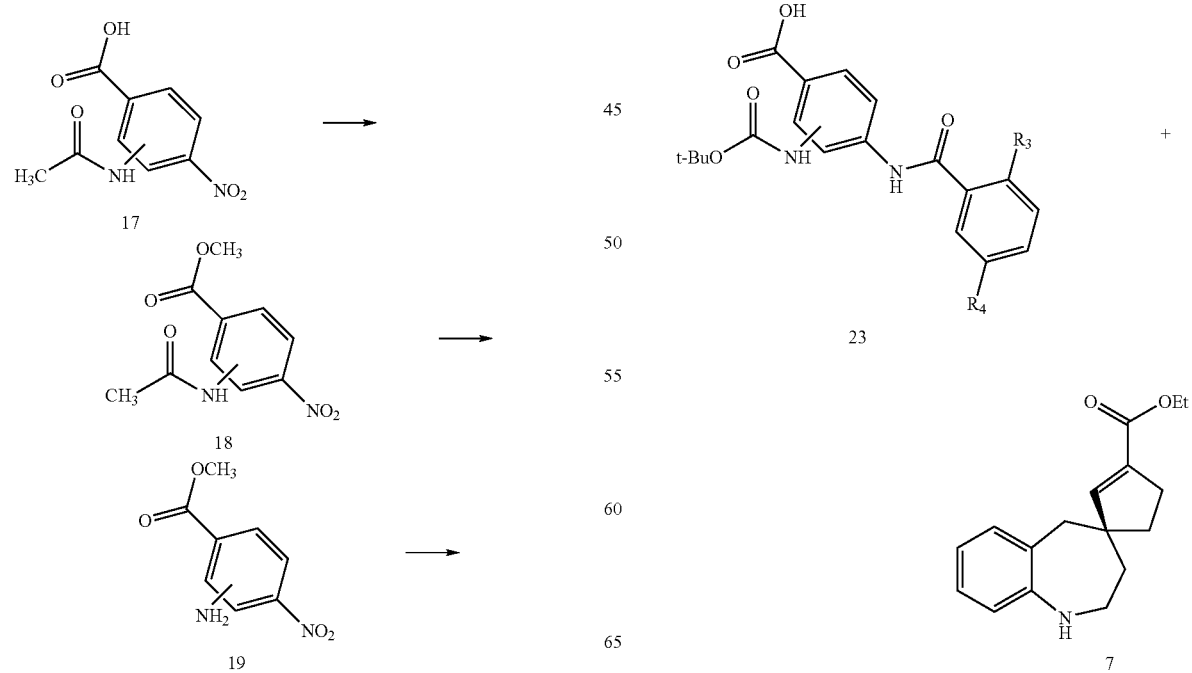

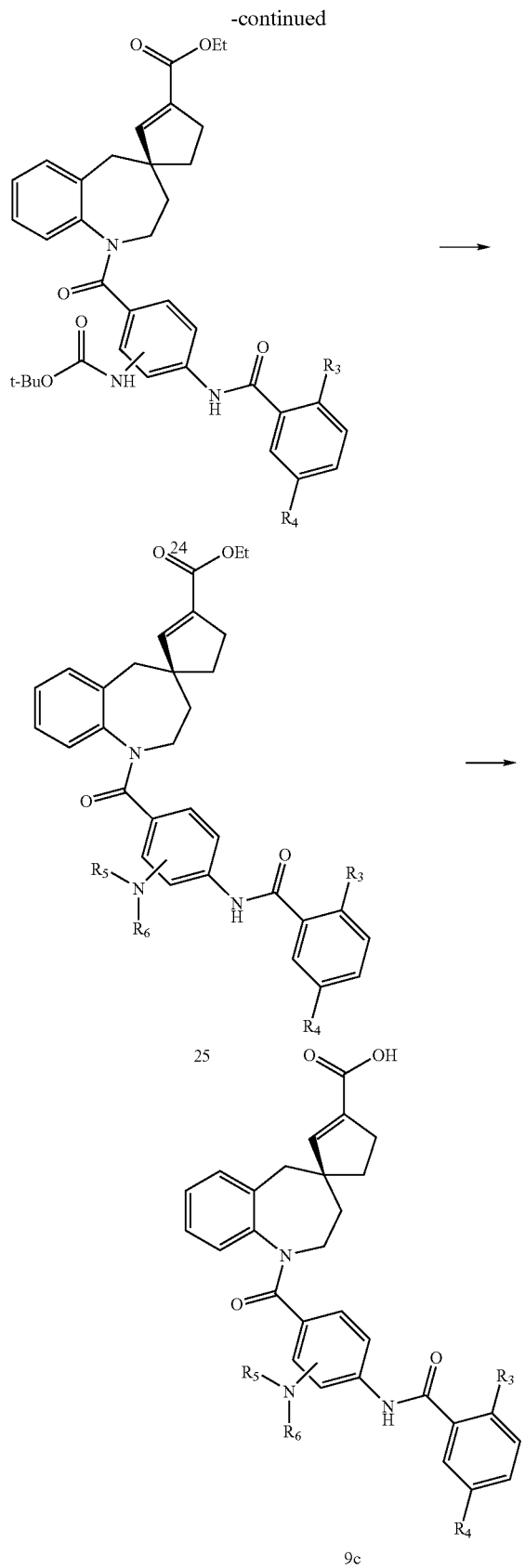

D. USE AND FORMULATIONS

The compounds of Formula I are useful in the treatment of conditions such as hypertension, hyponatremia, congestive heart failure/cardiac insufficiency, coronary vasospasm, cardiac ischemia, liver cirrhosis, renal vasospasm, renal failure, diabetic nephropathy, cerebral edema, cerebral ischemia, stroke, thrombosis, and water retention. Utility can be investigated according to the procedures known in the art, such as those described herein as Biological Examples 1-3 below. The present invention therefore provides a method of treating any of the above-disclosed conditions in a subject in need thereof, which method comprises administering a compound of Formula I in a pharmaceutically effective amount. The compound may be administered to a patient by any conventional route of administration including, but not limited to, intravenous, oral, subcutaneous, intramuscular, intradermal and parenteral.

The present invention also provides pharmaceutical compositions comprising one or more compounds, such two, three or four, of this invention in association with a pharmaceutically acceptable carrier.

To prepare the pharmaceutical compositions of this invention, one or more compounds of Formula I or, for example, a salt thereof, as an active ingredient(s), is intimately admixed with a pharmaceutical carrier according to conventional pharmaceutical compounding techniques. The form of the carrier depends upon the type of administration, e.g., oral, or parenteral such as intramuscular. In preparing the compositions in oral dosage form, any of the usual pharmaceutical media may be employed. Thus, for liquid oral preparations such as suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are generally employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1 mg to 1 g of active agent(s). Nonlimiting examples include 0.2 mg, 0.5 mg, 0.75 mg, 1 mg, 1.2 mg, 1.5 mg, 2 mg, 3 mg, 5 mg, 7 mg, 10 mg, 25 mg, 50 mg, 100 mg, 250 mg, and 500 mg dosages. The dosages, however, may be varied depending upon the requirement of the patients, the severity of the condition being treated and the compound being employed. The use of either daily administration or post-periodic dosing may be employed.

Preferably these compositions are in unit dosage form such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg or more of the active ingredient of the present invention. The tablets or pills of the disclosed compositions can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific or enantioselective synthesis, or by resolution. The compounds may, for example, be resolved into their components enantiomers by standard techniques, such as the formation of diastereomeric pairs by salt formation. The compounds may also be resolved by formation of diastereomeric esters or amides, followed by chromatographic separation and removal of the chiral auxiliary. Alternatively, the compounds may be resolved using a stereogenic HPLC column.

Advantageously, compounds of the present invention may be administered in a single daily dose, or the total daily dosage may be administered in divided doses of two, three or four times daily, once-weekly, biweekly, or once monthly. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms can be in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders of vascular resistance is required.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following examples are intended to illustrate the invention but not to limit it.

E. EXAMPLES

Example 1

(R)-3-Carboethoxy-4-aza-[6,4]-spiro-[5,6]-benzoundec-2'-ene (7)

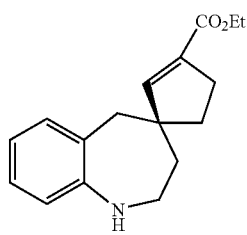

To a solution of (R)-spirobenzazepinecarboxylic acid (4 g, 16.5 mmol) in ethanol (200 mL) was added concentrated sulfuric acid (3.35 g, 33 mmol) and the resulting reaction mixture was allowed to stir at room temperature for 16 h. The reaction mixture was concentrated in vacuo and the residue taken up in dichloromethane (200 mL) washed with saturated sodium bicarbonate (200 mL) followed by saturated NaCl (200 mL) and the resulting dichloromethane extracts were dried over anhydrous sodium sulfate and concentrated in vacuo. Chromatography (SiO$_2$, 25% Ethyl Acetate-Hexanes eluent) provided 4.25 g of 7 as a clear oil (4.47 g theoretical, 95% yield). $^1$H NMR (CDCl$_3$) δ 7.0 (m, 2H), 6.8 (m, 1H), 6.7 (m, 1H), 6.6 (s, 1H), 4.25 (q, 2H), 3.15 (m, 1H), 3.05 (m, 1H), 2.9 (m, 1H), 2.7 (m, 1H), 1.8 (m, 4H). MS (ES) m/z 272 (MH)$^+$.

Example 2

(R)-4-(3-Methoxy-4-nitrobenzoyl)-4-aza-3'-(carboethoxy)-[6,4]-spiro-[5,6]-benzoundec-2'-ene (26)

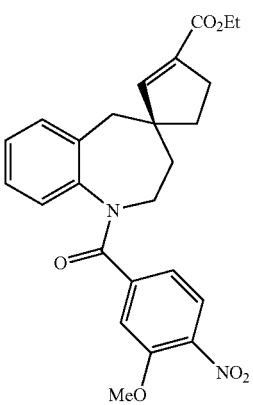

To a solution of the ester 7 (4.2 g, 15 mmol) and triethylamine (6 g, 60 mmol) in dichloromethane (200 mL) at 0° C. was added 4-nitro-3-methoxybenzoyl chloride (6.6 g, 30.7 mmol) and the resulting mixture was allowed to stir for 2 h with warming to room temperature. The reaction mixture was poured onto cold 1N sodium hydroxide and extracted with dichloromethane (2×200 mL). The combined dichloromethane extracts were washed with NaCl, dried over anhydrous sodium sulfate and concentrated in vacuo to provide 5.2 g of 26 as a clear oil (6.7 g theoretical, 77% yield). MS (ES) m/z 451 (MH)$^+$.

Example 3

(R)-4-(3-Methoxy-4-aminobenzoyl)-4-aza-3'-(carboethoxy)-[6,4]-spiro-[5,6]-benzoundec-2'-ene (27a) and (R)-4-(3-ethoxy-4-aminobenzoyl)-4-aza-3'-(carboethoxy)-[6,4]-spiro-[5,6]-benzoundec-2'-ene (27b)

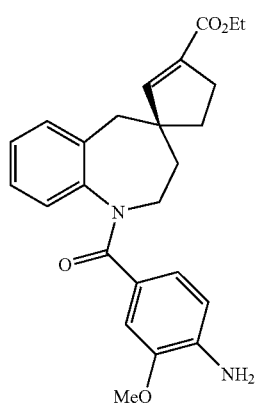

27a

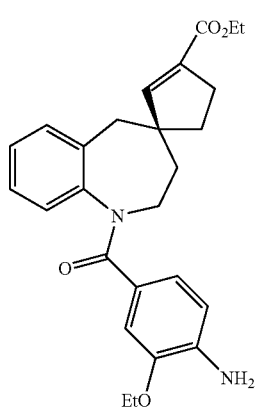

27b

To a solution of 26 (5.2 g, 11.5 mmol) in ethanol (200 mL) was added SnCl$_2$ (7.7 g, 38 mmol) and the resulting reaction mixture was allowed to stir at reflux for 16 h. The reaction mixture was quenched with saturated sodium bicarbonate (20 mL) and extracted with dichloromethane. The combined dichloromethane extracts were dried over anhydrous sodium sulfate and concentrated in vacuo. Chromatography (SiO$_2$, 50% Ethyl Acetate-Hexanes eluent) provided 1.5 g of 27a as an off white solid [MS (ES) m/z 421 (MH)$^+$ and 1 g of a yellow solid of 27b. MS (ES) m/z 435 (MH)$^+$.

Example 4

(R)-4-(2-Chloro-5-fluorobenzoyl-3-methoxy-4-aminobenzoyl)-4-aza-3'-(carboethoxy)-[6,4]-spiro-[5,6]-benzoundec-2'-ene (28)

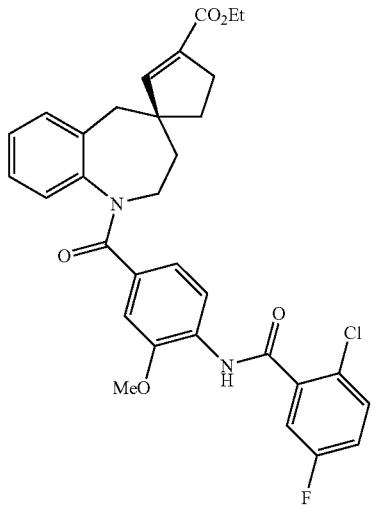

To a solution of 27a (4.16 g, 9.9 mmol) and triethylamine (5.5 mL, 39.6 mmol) in dichloromethane (400 mL) at room temperature was added 2-chloro-5-fluorobenzoyl chloride (2.85 g, 14.85 mmol) and the resulting reaction mixture was allowed to stir for 16 h. The reaction mixture was poured onto 1N NaOH (200 mL) and extracted with dichloromethane. The combined dichloromethane extracts were washed with saturated NaCl and dried over sodium sulfate and concentrated in vacuo. Chromatography (SiO$_2$, 50% Ethyl Acetate-Hexanes eluent) provided 2.26 g of 28 as a white foam (5.70 g theoretical, 40% yield). MS (ES) m/z 577 (MH)$^+$.

Example 5

(R)-4-(2-Chloro-5-fluorobenzoyl-3-methoxy-4-aminobenzoyl)-4-aza-3'-(carboxy)-[6,4]-spiro-[5,6]-benzoundec-2'-ene (29)

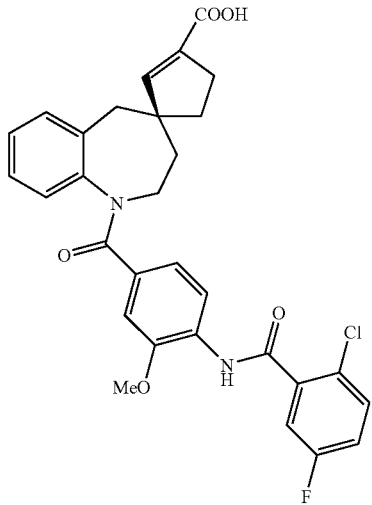

To a solution of the ethyl ester 28 (2.26 g, 3.92 mmol) in tetrahydrofuran (75 mL) at room temperature was added lithium hydroxide (1.2 g, 28.6 mmol) in water (50 mL) and the resulting reaction mixture was allowed to stir 24 h. The reaction mixture was poured onto 1N HCl (75 mL) and extracted with ethyl acetate (3×100 mL). The combined ethyl acetated extracts were washed with saturated NaCl and dried over anhydrous sodium sulfate and concentrated in vacuo to provide 1.75 g of 29 as a pale yellow solid (2.15 g theoretical, 81% yield). $^1$H NMR (CDCl$_3$) δ 8.7 (s, 1H), 8.25 (d, 1H), 7.5 (m, 1H), 7.4 (m, 1H), 7.3-7.1 (m, 2H), 7.0 (s, 1H), 6.95 (s, 1H), 6.7 (m, 1H), 4.9 (m, 1H), 3.7 (s, 3H), 3.1 (m, 1H), 2.7 (m, 3H), 2.1 (m, 2H), 1.75 (m, 2H). MS (ES) m/z 549 (MH)$^+$.

Example 6

(R)-4-(2-Chloro-5-fluorobenzoyl-3-ethoxy-4-aminobenzoyl)-4-aza-3'-(carboethoxy)-[6,4]-spiro-[5,6]-benzoundec-2'-ene (30)

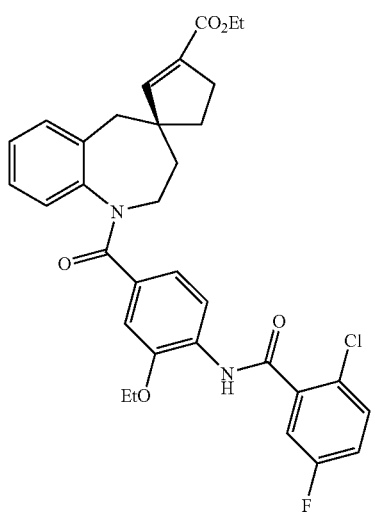

To a solution of 27b (434 mg, 1 mmol) and triethylamine (0.56 mL, 4 mmol) in dichloromethane (50 mL) at 0° C. was added 2-chloro-5-fluorobenzoyl chloride (229 mg, 1.5 mmol) and the resulting reaction mixture was allowed to stir for 2 h with warming to room temperature. The reaction mixture was poured onto 1N NaOH and extracted with dichloromethane (2×200 mL). The combined dichloromethane extracts were washed with saturated NaCl and dried over sodium sulfate and concentrated in vacuo to provide 500 mg of 30 as a white solid (591 mg theoretical, 85% yield). MS (ES) m/z 591 (M)$^+$.

Example 7

(R)-4-(2-Chloro-5-fluorobenzoyl-3-ethoxy-4-aminobenzoyl)-4-aza-3'-carboxy-[6,4]-spiro-[5,6]-benzoundec-2'-ene (31)

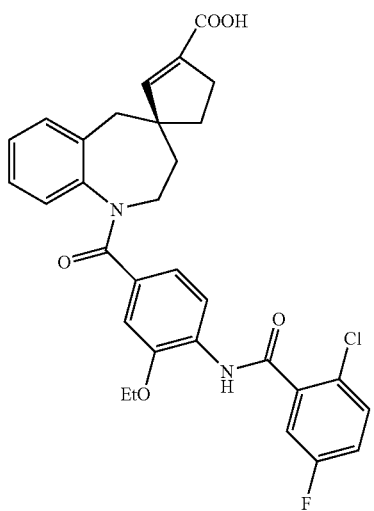

To a solution of the ethyl ester 30 (400 mg, 0.68 mmol) in tetrahydrofuran (25 mL) at room temperature was added lithium hydroxide (64.5 mg, 2.7 mmol) in water (25 mL) and the resulting reaction mixture was allowed to stir 16 h. The reaction mixture was poured onto 1N HCl (10 mL) and extracted with ethyl acetate (3×50 mL). The combined ethyl acetate extracts were washed with saturated NaCl and dried over anhydrous sodium sulfate and concentrated in vacuo to provide 300 mg of 31 as a waxy solid (381 mg theoretical, 79% yield). $^1$H NMR (CDCl$_3$) δ 8.95 (s, 1H), 8.25 (d, 1H), 7.6 (m, 1H), 7.4 (m, 1H), 7.2 (m, 1H), 7.1 (m, 1H), 7.0 (m, 1H), 6.95 (s, 1H), 6.85 (s, 1H), 6.7 (m, 1H), 6.55 (s, 1H), 4.85 (m, 1H), 3.95 (m, 2H), 3.3 (m, 1H), 3.15-2.9 (m, 1H), 2.8-2.6 (m, 3H), 2.15-1.95 (m, 2H), 1.8-1.5 (m, 2H). MS (ES) m/z 563 (MH)$^+$.

Example 8

3-Methoxy-4-nitro-benzoic acid methyl ester (32)

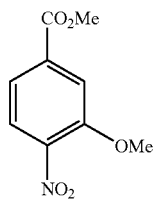

A 5-L, 3-necked, round-bottomed flask fitted with an overhead stirrer and a 250 mL addition funnel was charged with 3-hydroxy-4-nitrobenzoic acid (122 g, 0.66 mol), acetone (reagent grade, 1.5 L) and powdered K$_2$CO$_3$ (185 g). To this stirred suspension dimethylsulfate (127 mL) was added drop-wise. The suspension was stirred at room temperature for 18 h and filtered. The filtrate was concentrated under reduced pressure to about half the volume (ca 750 mL), transferred to a 3-L beaker and water (1-L) was added with stirring. The precipitated product was collected by filtration and dried in vacuum to obtain the title compound 32 as a white crystalline solid mp 87-88° C. $^1$H NMR (400 MHz, CDCl$_3$) δ: 7.77 (d, 1H), 7.68 (d, 1H), 7.63 (d, 1H), 3.94 (s, 3H), 3.90 (s, 3H). MS (ES) m/z 212.1 (MH)$^+$.

Example 9

4-Amino-3-methoxy-benzoic acid methyl ester (33)

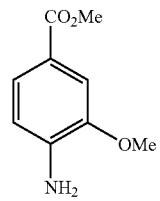

A 2-L, Parr high-pressure hydrogenation bottle (glass rated to 80 psi) was charged with Pd/C (10 wt % on Carbon, 5 g), ethyl acetate (800 mL) and 32 (120.5 g, 0.57 mol). The reaction mixture was charged with H$_2$ (30 psi) on a Parr apparatus. Charging H$_2$ was continued carefully several times until the pressure remained steady. This took approximately about 3 h. The reaction was shaken for an additional 0.5 h. After the hydrogenation, the reaction mixture was diluted with ethyl acetate to dissolve some of the precipitated product and directly passed through a short pad of Celite, and washed with ethyl acetate. The solvent was evaporated to yield 4-amino-3-methoxy-benzoic acid methyl ester 33 as a white solid. $^1$H NMR (400 MHz, CDCl$_3$) δ: 7.55 (dd, 1H), 7.45 (d, 1H), 6.66 (d, 1H), 4.21 (s, 2H), 3.90 (s, 3H), 3.86 (s, 3H). MS (ES) m/z 182.1 (MH)$^+$.

Example 10

4-(2-Chloro-5-fluoro-benzoylamino)-3-methoxy-benzoic acid methyl ester (34)

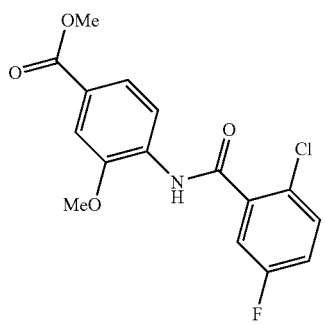

A dry, 3-L, 3-necked, round-bottomed flask equipped with a thermometer and addition funnel was charged a solution of 33 (96 g, 0.53 mol, 1.0 equiv.) and Et$_3$N (88 ml, 0.64 mol, 1.2 equiv.) in dichloromethane (1.2 L). The solution was cooled to 0° C. by an ice bath and 2-chloro-5-fluoro-benzoyl chloride (110 g, 0.57 mol, 1.05 equiv.) was added drop-wise over 40 min at 0° C. After the addition, the reaction mixture was stirred at 0° C. for further 1.5 h. The organic layer was washed with brine three times, dried over MgSO$_4$, filtered, and evaporated to yield 4-(2-chloro-5-fluoro-benzoylamino)-3-methoxy-benzoic acid methyl ester 34 as a white solid. $^1$H NMR (400 MHz, CDCl$_3$) δ: 8.84 (s, 1H), 8.61 (d, 1H), 7.75 (dd, 1H), 7.60 (d, 1H), 7.55 (dd, 1H), 7.45 (dd, 1H), 7.20-7.13 (m, 1H), 3.97 (s, 3H), 3.93 (s, 3H). MS (ES) m/z 338.0 (MH)$^+$.

Example 11

4-(2-Chloro-5-fluoro-benzoylamino)-3-methoxy-benzoic acid (35)

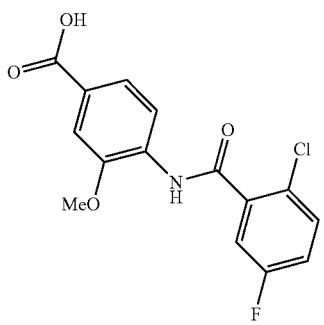

LiOH (14.1 g, 0.59 mol, 1.1 equiv.) dissolved in H$_2$O (200 mL) was added drop-wise over 45 minutes to a solution of 34 (180 g, 0.53 mol, 1 equiv.) in tetrahydrofuran (1800 mL) at room temperature. The reaction mixture was stirred at room temperature for 16 h. The solvent was evaporated under reduced pressure and the residue re-dissolved in water (ca. 3 L). The insoluble solid was filtered off. Under vigorous stirring, the aqueous filtrate solution was acidified with concentrated HCl aqueous solution (37%) until pH<2. The resulting white solid precipitate was filtered and washed with water. The wet filter cake was then transferred to a flask and dried on rotary evaporator under vacuum at 50° C. overnight to yield 4-(2-chloro-5-fluoro-benzoylamino)-3-methoxy-benzoic acid 35 as a dry, fine white powder. $^1$H NMR (400 MHz, DMSO-d6) δ: 12.90 (s, 1H), 10.01 (s, 1H), 8.22 (d, 1H), 7.65-7.45 (m, 4H), 7.45-7.30 (m, 1H), 3.88 (s, 1H). MS (ES) m/z 322.0 (MH)$^+$.

Example 12

4-(2-Chloro-5-fluoro-benzoylamino)-3-methoxy-benzoyl chloride (36)

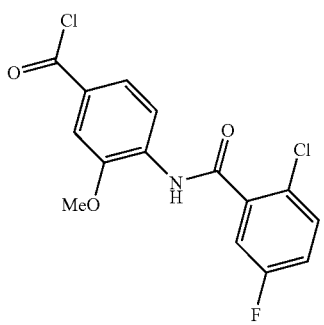

35 (152 g, 0.45 mol, 1 equiv.) was suspended in dichloromethane (1.5 L) and dimethylformamide (1 mL) was added. Oxalyl chloride (71.6 g, 0.56 mol, 1.2 equiv.) was added drop-wise over 30 minutes at 0° C. After addition, the cold bath was removed and the reaction mixture was further stirred at room temperature for 3.5 h. The solvent and any unreacted oxalyl chloride were evaporated to yield a white solid, which was further dried on a rotary evaporator under vacuum at 40° C. overnight to yield dry 4-(2-chloro-5-fluoro-benzoylamino)-3-methoxy-benzoyl chloride 36 as a white solid. $^1$H NMR (400 MHz, CDCl$_3$) δ: 8.97 (s, 1H), 8.71 (d, 1H), 7.91 (dd, 1H), 7.60 (d, 1H), 7.57 (dd, 1H), 7.47 (dd, 1H), 7.21-7.15 (m, 1H), 3.99 (s, 3H). MS (ES) m/z 339.9 (MH)$^+$.

In a manner analogous to the process outlined in Example 12, 4-(2-chloro-5-fluoro-benzoylamino)-3-methoxy-benzoic acid was suspended in dichloroethane and reacted to yield the 4-(2-chloro-5-fluoro-benzoylamino)-3-methoxy-benzoyl chloride as a white solid.

Example 13

(R)-1,2,3,5-tetrahydro-spiro[4H-1-benzazepine-4,1'-[2]cylopentene]-3'-carboxylic acid (37)

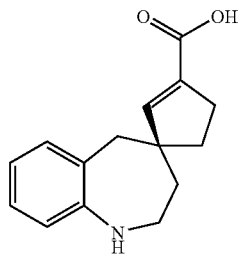

In a 3-necked, 5-L, round-bottomed flask fitted with an air-pump stirrer, (4R)-2,3,4,5-tetrahydrobenzazepine-4-spiro-3'-cyclopent-1'-ene-carboxylic acid-(1R,4S)-7,7-dimethyl-2-oxo-bicyclo[2.2.1]heptane-methanesulfonate (500 g, 1.05 mol) was suspended in water (2 L) to yield a reaction mixture with a pH of about 3-4. With an addition funnel, saturated aqueous NaHCO$_3$ solution was added slowly to the mixture until pH 6. Dichloromethane (1 L) was then added and the slurry mixture stirred for 1 h. Any remaining starting material in the mixture was then filtered off. The layers were separated and the aqueous layer extracted with dichloromethane (2×150 mL). The combined organic layer was dried with Na$_2$SO$_4$, filtered and concentrated to yield (4R)-1,2,3,5-tetrahydro-spiro[4H-1-benzazepine-4,1'-[2]cylopentene]-3'-carboxylic acid (37) as a dark gray solid. To the remaining starting material, the process was repeated again until all the salts were completely converted to free acid. All of crude (4R)-1,2,3,5-tetrahydro-spiro[4H-1-benzazepine-4,1'-[2]cylopentene]-3'-carboxylic acid was combined, suspended in ethyl acetate/hexanes (1:1) stirring overnight at room temperature and then filtered to yield (4R)-1,2,3,5-tetrahydro-spiro[4H-1-benzazepine-4,1'-[2]cylopentene]-3'-carboxylic acid 37 as a gray solid in 88% yield. $^1$H NMR (400 MHz, CDCl$_3$) δ: 7.09-7.01 (m, 2H), 6.76 (t, 1H), 6.77 (s, 1H), 6.72 (d, 1H), 3.17-3.14 (m, 1H), 3.07-3.05 (m, 1H), 2.82 (dd, 2H), 2.71-2.54 (m, 2H), 1.92-1.68 (m, 4H). MS (ES) m/z 244.1 (MH)$^+$.

Example 14

(R)-4-(3-Isopropoxy-4-aminobenzoyl)-4-aza-3'-(carboethoxy)-[6,4]-spiro-[5,6]-benzoundec-2'-ene (38)

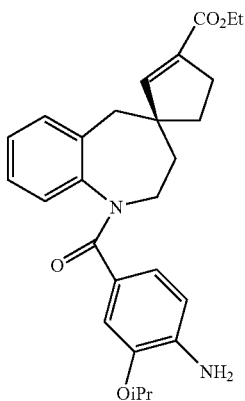

To a solution of nitro compound 7 (200 mg, 0.34 mmol) in isopropanol (50 mL) was added SnCl$_2$ (128 mg, 0.68 mmol) and the resulting reaction mixture was allowed to stir at reflux for 16 h. The reaction mixture was quenched with saturated sodium bicarbonate (20 mL) and extracted with dichloromethane. The combined dichloromethane extracts were dried over anhydrous sodium sulfate and concentrated in vacuo. Chromatography (SiO$_2$, Ethyl acetate eluent) provided 56 mg of 38 as an off white solid (190 mg theoretical, 30% yield). MS (ES) m/z 449 (MH)$^+$.

Example 15

(R)-4-(2-Chloro-5-fluorobenzoyl-3-isopropoxy-4-aminobenzoyl)-4-aza-3'-(carbomethoxy)-[6,4]-spiro-[5,6]-benzoundec-2'-ene (39)

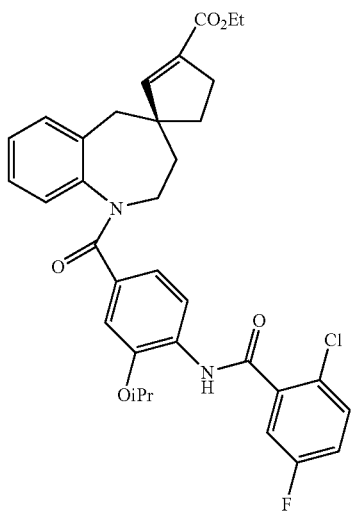

To a solution of 38 (50 mg, 0.12 mmol) and triethylamine (0.08 mL, 0.6 mmol) in dichloromethane (25 mL) at room temperature was added 2-chloro-5-fluorobenzoyl chloride (39 mg, 0.23 mmol) and the resulting reaction mixture was allowed to stir for 16 h. The reaction mixture was poured onto 1N NaOH (50 mL) and extracted with dichloromethane. The combined dichloromethane extracts were washed with saturated NaCl and dried over sodium sulfate and concentrated in vacuo. Chromatography (SiO$_2$, 50% Ethyl acetate-Hexanes eluent) provided 80 mg of 39 as a white foam taken onto the next step without further purification.

Example 16

(R)-4-(2-Chloro-5-fluorobenzoyl-3-isopropoxy-4-aminobenzoyl)-4-aza-3'-(carboxy)-[6,4]-spiro-[5,6]-benzoundec-2'-ene (40)

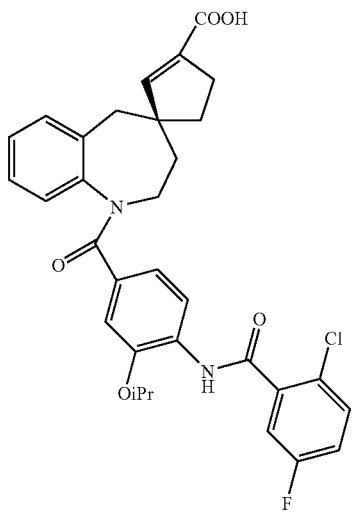

To a solution of the ethyl ester 39 (80 mg, 0.15 mmol) in tetrahydrofuran (10 mL) at room temperature was added lithium hydroxide (18 mg, 0.75 mmol) in water (10 mL) and the resulting reaction mixture was allowed to stir 24 h. The reaction mixture was poured onto 1N HCl (25 mL) and extracted with ethyl acetate (3×50 mL). The combined ethyl acetated extracts were washed with saturated NaCl and dried over anhydrous sodium sulfate and concentrated in vacuo to provide 51 mg of 40 as a pale yellow solid (64 mg theoretical, 80% yield). $^1$H NMR (CDCl$_3$) δ 8.7 (s, 1H), 8.25 (d, 1H), 7.5 (m, 1H), 7.4 (m, 1H), 7.3-7.1 (m, 2H), 7.0 (s, 1H), 6.95 (s, 1H), 6.7 (m, 1H), 4.9 (m, 1H), 4.4 (m, 1H), 3.1 (m, 1H), 2.7 (m, 3H), 2.1 (m, 2H), 1.75 (m, 2H), 1.3 (d, 3H), 1.1 (d, 3H). MS (ES) m/z 577 (MH)$^+$.

Biological Example 1

(A) In-Vitro Binding Assay

Assay buffer is 50 mM Tris-Cl, 5 mM MgCl$_2$, 0.1% BSA (pH 7.5) containing 5 μg/ml of aprotinin, leupeptin, pepstatin, 50 μg/ml bacitracin, and 1 mM Pefabloc (4-(2-Aminoethyl)-benzenesulfonyl fluoride, hydrochloride manufactured by Roche Diagnostics Corporation, Indianapolis, Ind. and distributed by Boehringer Mannheim). H3 vasopressin is $^3$H-arginine-8-vasopressin (NEN Life Sciences, Boston, Mass.; 68.5 Ci/mmol, final concentration in assay is 0.65-0.75 nM). Into wells of 96-well round bottom polypropylene plates are added buffer, test compound, membrane (containing human V1a or V2 receptor), and H3 vasopressin. The reaction plates are allowed to sit at room temperature for one hour. The samples are filtered through Unifilter GF/C plates (PerkinElmer Life Sciences, Boston, Mass.) presoaked in 0.3 polyethyleneimine. The plates are washed 5 times with cold physiological saline containing 0.05% Tween 20. After drying, the bottom of the filter plates are sealed and 0.025 ml of Microscint-20 (Packard Instrument Co, Meriden, Conn.) is added to each filter. The top of the plate is sealed, and the plate is counted. Non-specific binding is determined by the addition of 1.25 µM arginine-8-vasopressin in those wells. % Inh. is calculated $$\% \text{ inhibition} = 100 - 100 \times \frac{\text{peak response after drug}}{\text{peak response before drug}}$$

as follows:

(B) V1a Vasopressin Receptor Functional Activity

The V1a receptor is a G-protein coupled receptor, which upon activation triggers an increase in intracellular calcium mobilization. To evaluate compounds for their functional V1a receptor activity, HEK-293 cells were transfected with the human V1a receptor (V1a-HEK cells). HEK-293 cells were grown in DMEM (Dulbecco's modified Eagle Media) supplemented with 10% FBS and glutamine. HEK-cells were passed biweekly by trypsinization and seeded into 96 well plates at 33,000 cells per well. HEK-293 cells were transfected with human V1a receptor DNA using DMRIE-C reagent from Life Technologies (Carlsbad, Calif.). Stable lines were generated by selecting cells grown in culture media containing geneticin. After growing in Packard Clear-View black 96 well plates for 4-6 days, V1a-HEK cells were loaded with the calcium-sensitive fluorescence dye, FLUO-3 AM. Changes in intracellular calcium mobilization were measured by quantitating intracellular fluorescence using FLIPR (Fluorometric Imaging Plate Reader; Molecular Devices, Sunnyvale, Calif.). Test compounds were first added to the cells and the resulting changes in fluorescence measured to detect receptor agonistic activity. Five minutes later the cells were challenged with vasopressin to test compounds for their antagonistic activity. Receptor antagonists inhibit the ability of vasopressin to stimulate increases in intracellular fluorescence. $IC_{50}$'s were calculated.

Biological Example 2

V2 Vasopressin Receptor Functional Activity

The V2 receptor is also a G-protein coupled receptor which when activated induces an increase in cAMP turnover. Antagonism against the V2 receptor is determined by measuring cAMP accumulation in transfected HEK-293 cells expressing the human V-2 receptor (V2-HEK cells). Compounds are tested for their ability to block the stimulatory effects of vasopressin on cAMP accumulation. The cell content of cAMP is measured by radioimmunoassay using NEN flashplates.

Biological Example 3

Reversal of Vasopressin-Induced Hypertension in Rats

The anti-hypertensive activity of a compound may be assessed using an anesthetized model of vasopressin-induced hypertension. Male Long Evans, normotensive rats of between 350 and 450 g in body weight may be anesthetized with pentobarbital (35 mg/kg, ip) and maintained throughout the procedure with an ip infusion of 10 mg/kg/hr. Arginine vasopressin (AVP) can be infused at 30 ng/kg/min, iv, to induce a stable hypertensive state (ca. 50 mm Hg increase in mean arterial blood pressure). Compounds of interest can be administered in an ascending dose fashion and the maximum decrease in mean arterial blood pressure can be recorded. An $ED_{50}$ may be determined from the linear portion of the dose-response relationship for each animal.

Biological Example 4

Several animal models are believed to mimic various components of diabetic nephropathy in humans, in particular, the streptozotocin-induced model of type 1 diabetes in rats, the db/db genetic mouse model of type 2 diabetes and the 5/6 nephrectomy model of renal failure in rats. JNJ-17158063 will be initially evaluated in the streptozotocin diabetic model by administering the compound at 1, 3 or 10 mg/kg/day for 12 weeks and monitoring several endpoints during the study that are indicative of diabetic kidney disease, including reduced urine albumin, serum creatinine levels and levels of various cytokines in urine. At the end of the study, morphologic changes in the kidney will be evaluated histologically for comparison to normal kidneys. Similar studies will be performed in the other two models to confirm activity.

Biological Example 5

Argenine-vasopressin (AVP) levels are dramatically elevated following ischemic stroke and head injury and contribute to the tissue inflammatory response. AVP receptor antagonists have been shown to block development of cerebral edema following traumatic brain injury and ischemic stroke by regulating water and electrolyte transport across the cerebrovascular endothelium (via endothelial V1a receptor inhibition) and by promoting diuresis (via renal V2 receptors). Additional neuroprotective actions of AVP receptor antagonists may be mediated by inhibition of neuronal V1a receptors. Thus, compounds of this invention may be useful in ischemic stroke and traumatic brain injury. V1a/V2 antagonists may reduce the post-ischemia inflammatory response and reduce the volume of brain tissue infarction following ischemic stroke. As many of the neuroprotective and anti-edema actions of AVP receptor antagonists are mediated at the level of the cerebrovascular endothelium or kidney, it is not essential that lead compounds cross the blood brain barrier. However, as noted above, CNS penetration may add benefit by limiting actions of AVP at neuronal V1a receptors.

The pharmacokinetic properties of a compound may be determined in order to optimize plasma half-life and optimal dosing regimen. This includes evaluation the ability of these compounds to cross the blood-brain barrier, and direct measurement of drug concentrations and half-life in brain tissue. The neuroprotective and anti-edema properties of these compounds can be determined with a rodent model of embolic stroke. In this model, an aliquot of the animal's blood is removed and refrigerated overnight to allow a thrombin-rich clot to form. This clot is then placed surgically at the origin of the middle cerebral artery and left in place for 2-4 hrs to produce prolonged cerebral ischemia. At this point the clot may be left in place permanently or the clot may be lysed using intravenous administration of recombinant tissue plasminogen activator (rt-PA) to allow reperfusion. The vasopressin receptor antagonists of this invention may be administered intravenously at various times following clot placement and may be given as a bolus dose, a bolus dose followed by continuous intravenous infusion or continuous intravenous infusion alone. Compound may be given at times ranging from two hours to one week following onset of ischemia to define the optimal treatment window. The acute intravenous dosing may also be followed by oral administration of the compound to determine the optimal treatment duration.

The vasopressin receptor antagonists of this invention may be profiled in a rodent model of traumatic brain injury. This model requires opening a cranial window to exposed the dura matter. A controlled, measured weight is then dropped on the dura to induce injury. This model is well characterized and produces a defined pattern of neuronal cell loss and inflammation.

Edema, inflammation and neuroprotection may be determined using one or more of the following approaches: Animals may be euthanized at various time points following ischemia, from 24 hrs to four weeks, and the volume of infarction and brain edema may be measured using standard histological and histochemical methods. Animals may also be subjected to MRI imaging so that the evolution of infarction and edema can be measured within the same animal. Finally, histological and histochemical measurements of blood-brain barrier integrity and infiltration of inflammatory cells (e.g., monocytes, macrophages, microglial cells) may be performed and used for quantitative analyses.

Finally, all animals may be evaluated in a comprehensive series of behavioral assays to evaluate the effects of vasopressin receptor antagonists on neurological function and behavior. These behavioral assessments may include a global neurological assessment, evaluation of motor asymmetry and assessment of sensorimotor integration using assays such as the foot-fault, Rotarod and beam-balance tests.

Data is shown below in Table I, where the values are for V1a/V2. Racemic structure A is 4-(2-phenylbenzoyl-4-aminobenzoyl)-3'-[2-(N,N-dimethylaminoethylcarbony)]-4-aza-[6,4]-spiro-[5,6]-benzoundec-2'-ene published in WO 02/02531 A1, p. 43, compound 9.

|  | A |  | Compound 29 | Compound 31 |
|---|---|---|---|---|
| Binding IC$_{50}$ (μM) | 0.005/0.011 | 0.013/0.053 | 0.005/0.030 | 0.008/0.071 |
| Functional IC$_{50}$ (μM) | 0.004/— | 0.38/0.10 | 0.038/0.052 | 0.05/0.15 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula I:

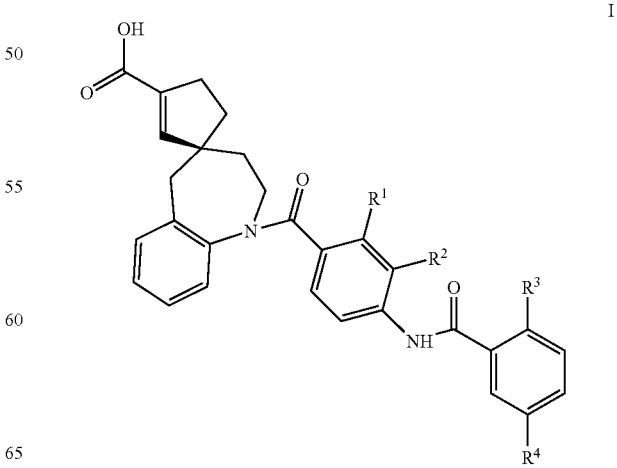

wherein
one of $R^1$ and $R^2$ is H and the other is H, $NR^5R^6$, $C_{1-6}$ alkoxy, hydroxy, or halo; wherein each of $R^5$ and $R^6$ is independently H or $C_{1-3}$ alkyl;
$R^3$ is chloro;
$R^4$ is chloro, fluoro, methoxy, or methyl;
or a pharmaceutically acceptable $C_{1-6}$ ester, $C_{1-6}$ amide, or di($C_{1-6}$ alkyl)amide or salt thereof.

2. A compound of claim 1, wherein $R^2$ is amino.
3. A compound of claim 1, wherein $R^2$ is $C_{1-4}$ alkoxy.
4. A compound of claim 3, wherein $R^2$ is methoxy, ethoxy, propoxy, isopropoxy, butoxy, isobutoxy, or t-butoxy.
5. A compound of claim 4, wherein $R^2$ is methoxy or ethoxy.
6. A compound of claim 1, wherein $R^4$ is fluoro, chloro, or methyl.
7. A compound of claim 6, wherein $R^4$ is fluoro or chloro.
8. A compound of claim 7, wherein $R^4$ is fluoro.
9. A compound of claim 7, wherein $R^2$ is methoxy or ethoxy.
10. A compound of claim 1, wherein $R^1$ is H.
11. A compound of claim 10, wherein $R^2$ is methoxy or ethoxy and $R^4$ is fluoro.
12. A compound of claim 1, selected from:
(R)-4-(2-Chloro-5-fluorobenzoyl-3-methoxy-4-aminobenzoyl)-4-aza-3'-(carboxy)-[6,4]-spiro-[5,6]-benzoundec-2'-ene
(R)-4-(2-Chloro-5-fluorobenzoyl-3-ethoxy-4-aminobenzoyl)-4-aza-3'-(carboxy)-[6,4]-spiro-[5,6]-benzoundec-2'-ene
(R)-4-(2-Chloro-5-fluorobenzoyl-3-isopropoxy-4-aminobenzoyl)-4-aza-3'-(carboxy)-[6,4]-spiro-[5,6]-benzoundec-2'-ene
(R)-4-(2-Chloro-5-fluorobenzoyl-3-hydroxy-4-aminobenzoyl)-4-aza-3'-(carboxy)-[6,4]-spiro-[5,6]-benzoundec-2'-ene
(R)-4-(2-Chloro-5-fluorobenzoyl-4-aminobenzoyl)-4-aza-3'-(carboxy)-[6,4]-spiro-[5,6]-benzoundec-2'-ene
(R)-4-(2-Chloro-5-fluorobenzoyl-3-amino-4-aminobenzoyl)-4-aza-3'-(carboxy)-[6,4]-spiro-[5,6]-benzoundec-2'-ene
(R)-4-(2-Chloro-5-fluorobenzoyl-3-chloro-4-aminobenzoyl)-4-aza-3'-(carboxy)-[6,4]-spiro-[5,6]-benzoundec-2'-ene
(R)-4-(2-Chloro-5-fluorobenzoyl-2-chloro-4-aminobenzoyl)-4-aza-3'-(carboxy)-[6,4]-spiro-[5,6]-benzoundec-2'-ene
(R)-4-(2-Chloro-5-fluorobenzoyl-2-amino-4-aminobenzoyl)-4-aza-3'-(carboxy)-[6,4]-spiro-[5,6]-benzoundec-2'-ene
(R)-4-(2-Chloro-5-fluorobenzoyl-2-hydroxy-4-aminobenzoyl)-4-aza-3'-(carboxy)-[6,4]-spiro-[5,6]-benzoundec-2'-ene
(R)-4-(2-Chloro-5-fluorobenzoyl-2-methoxy-4-aminobenzoyl)-4-aza-3'-(carboxy)-[6,4]-spiro-[5,6]-benzoundec-2'-ene
(R)-4-(2-Chloro-5-methyl benzoyl-3-methoxy-4-aminobenzoyl)-4-aza-3'-(carboxy)-[6,4]-spiro-[5,6]-benzoundec-2'-ene
(R)-4-(2-Chloro-5-methyl benzoyl-3-hydroxy-4-aminobenzoyl)-4-aza-3'-(carboxy)-[6,4]-spiro-[5,6]-benzoundec-2'-ene
(R)-4-(2-Chloro-5-methyl benzoyl-4-aminobenzoyl)-4-aza-3'-(carboxy)-[6,4]-spiro-[5,6]-benzoundec-2'-ene
(R)-4-(2-Chloro-5-methyl benzoyl-3-amino-4-aminobenzoyl)-4-aza-3'-(carboxy)-[6,4]-spiro-[5,6]-benzoundec-2'-ene
(R)-4-(2-Chloro-5-methyl benzoyl-3-chloro-4-aminobenzoyl)-4-aza-3'-(carboxy)-[6,4]-spiro-[5,6]-benzoundec-2'-ene
(R)-4-(2-Chloro-5-methoxybenzoyl-3-methoxy-4-aminobenzoyl)-4-aza-3'-(carboxy)-[6,4]-spiro-[5,6]-benzoundec-2'-ene
(R)-4-(2-Chloro-5-methoxybenzoyl-3-hydroxy-4-aminobenzoyl)-4-aza-3'-(carboxy)-[6,4]-spiro-[5,6]-benzoundec-2'-ene
(R)-4-(2-Chloro-5-methoxybenzoyl-4-aminobenzoyl)-4-aza-3'-(carboxy)-[6,4]-spiro-[5,6]-benzoundec-2'-ene
(R)-4-(2-Chloro-5-methoxybenzoyl-3-amino-4-aminobenzoyl)-4-aza-3'-(carboxy)-[6,4]-spiro-[5,6]-benzoundec-2'-ene
(R)-4-(2-Chloro-5-methoxybenzoyl-3-chloro-4-aminobenzoyl)-4-aza-3'-(carboxy)-[6,4]-spiro-[5,6]-benzoundec-2'-ene
(R)-4-(2,5-Dichlorobenzoyl-3-methoxy-4-aminobenzoyl)-4-aza-3'-(carboxy)-[6,4]-spiro-[5,6]-benzoundec-2'-ene
(R)-4-(2,5-Dichlorobenzoyl-3-hydroxy-4-aminobenzoyl)-4-aza-3'-(carboxy)-[6,4]-spiro-[5,6]-benzoundec-2'-ene
(R)-4-(2,5-Dichlorobenzoyl-4-aminobenzoyl)-4-aza-3'-(carboxy)-[6,4]-spiro-[5,6]-benzoundec-2'-ene
(R)-4-(2,5-Dichlorobenzoyl-3-amino-4-aminobenzoyl)-4-aza-3'-(carboxy)-[6,4]-spiro-[5,6]-benzoundec-2'-ene; and
(R)-4-(2,5-Dichlorobenzoyl-3-chloro-4-aminobenzoyl)-4-aza-3'-(carboxy)-[6,4]-spiro-[5,6]-benzoundec-2'-ene.

13. A compound of claim 1, selected from

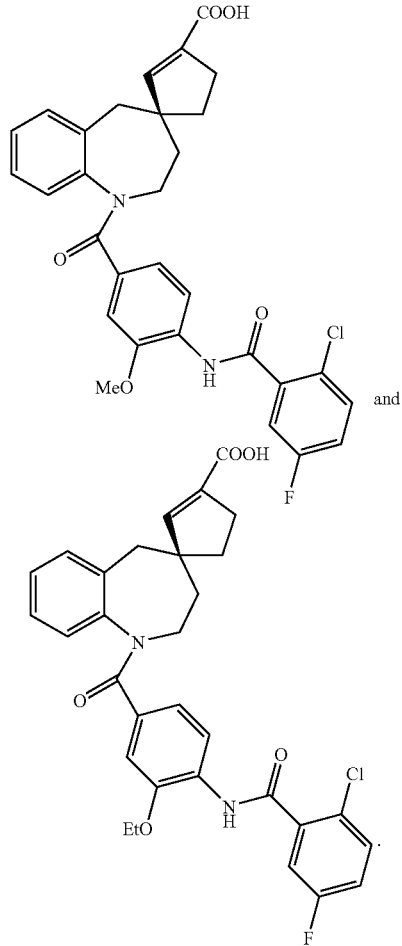

14. A compound of claim 1, which is

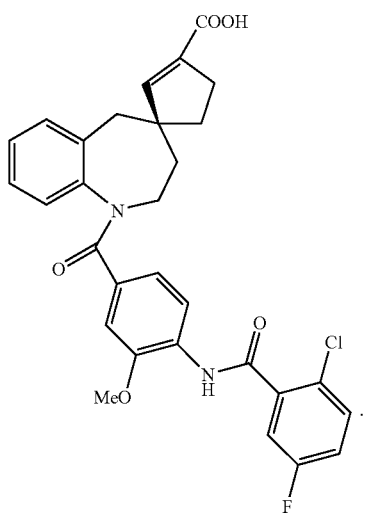

15. A compound of claim 1, which is

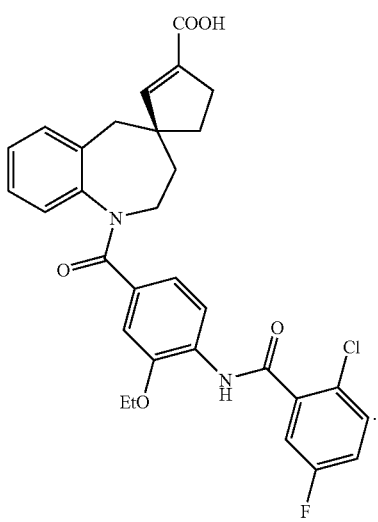

16. A pharmaceutical composition comprising a compound according to claim 1 and a pharmaceutically acceptable carrier.

17. A method of treating a subject suffering from a condition associated with vasopressin receptor activity, which comprises administering to the subject a therapeutically effective amount of the compound of Formula I as defined in claim 1, wherein said condition is selected from inner ear disorders, hypertension, congestive heart failure, cardiac insufficiency, coronary vasospasm, cardiac ischemia, liver cirrhosis, renal vasospasm, renal failure, diabetic nephropathy, hyponatremia, cerebral edema, cerebral ischemia, stroke, thrombosis, water retention, aggression, obsessive-compulsive disorders, dysmenorrhea, nephrotic syndrome, anxiety and central nervous injuries.

18. A method of inhibiting in a subject the onset or progression of a condition associated with vasopressin receptor activity, which comprises administering to the subject a prophylactically-effective dose of a compound of Formula I as defined in claim 1, wherein said condition is selected from inner ear disorders, hypertension, congestive heart failure, cardiac insufficiency, coronary vasospasm, cardiac ischemia, liver cirrhosis, renal vasospasm, renal failure, diabetic nephropathy, hyponatremia, cerebral edema, cerebral ischemia, stroke, thrombosis, water retention, aggression, obsessive-compulsive disorders, dysmenorrhea, nephrotic syndrome, anxiety and central nervous injuries.

19. The method of claim 18 wherein said condition is congestive heart failure, or cardiac insufficiency.

20. The method of claim 18, wherein said condition is hyponatremia.

21. The method of claim 18 wherein said condition is hypertension.

22. A process for making a pharmaceutical composition comprising mixing any of the compounds according to claim 1 and a pharmaceutically acceptable carrier.

* * * * *

UNITED STATES PATENT AND TRADEMARK OFFICE
CERTIFICATE OF CORRECTION

PATENT NO.       : 7,687,494 B2                                         Page 1 of 1
APPLICATION NO. : 11/735149
DATED            : March 30, 2010
INVENTOR(S)      : Patel et al.

It is certified that error appears in the above-identified patent and that said Letters Patent is hereby corrected as shown below:

Column 37
Line 54, delete "methyl benzoly", and insert -- methylbenzoly --

Line 57, delete "methyl  benzoly", and insert -- methylbenzoly --

Line 60, delete "methyl  benzoly", and insert -- methylbenzoly --

Line 62, delete "methyl benzoly", and insert -- methylbenzoly --

Line 65, delete "methyl benzoly", and insert -- methylbenzoly --

Signed and Sealed this

Second Day of November, 2010

David J. Kappos
*Director of the United States Patent and Trademark Office*